United States Patent
Magness

(10) Patent No.: US 12,213,906 B2
(45) Date of Patent: Feb. 4, 2025

(54) DENTAL APPLIANCE FOR TREATMENT OF SLEEP APNEA

(71) Applicant: R. Joseph Magness, Orem, UT (US)

(72) Inventor: R. Joseph Magness, Orem, UT (US)

(*) Notice: Subject to any disclaimer, the term of this patent is extended or adjusted under 35 U.S.C. 154(b) by 0 days.

(21) Appl. No.: 14/808,807

(22) Filed: Jul. 24, 2015

(65) Prior Publication Data

US 2016/0022474 A1    Jan. 28, 2016

Related U.S. Application Data

(63) Continuation-in-part of application No. 14/321,648, filed on Jul. 1, 2014, now Pat. No. 10,080,680.

(60) Provisional application No. 62/028,860, filed on Jul. 25, 2014, provisional application No. 61/901,696, (Continued)

(51) Int. Cl.
    *A61F 5/56*    (2006.01)
(52) U.S. Cl.
    CPC ........ *A61F 5/566* (2013.01); *A61F 2005/563* (2013.01)
(58) Field of Classification Search
    CPC ...... A61F 5/56; A61F 5/566; A61F 2005/563; A61C 7/08; A61C 7/36; A61C 7/00; A61C 7/10; A61C 11/00; A61C 11/001; A61C 11/003; A61C 11/005; A61C 11/006; A61C 11/008; A61C 19/00; A63B 71/085
    See application file for complete search history.

(56) References Cited

U.S. PATENT DOCUMENTS

| 4,305,709 A | 12/1981 | Bruhn et al. |
| 5,427,117 A * | 6/1995 | Thornton ................ A61F 5/566 128/848 |
| 5,683,244 A | 11/1997 | Truax |

(Continued)

FOREIGN PATENT DOCUMENTS

ES    2542577    6/2015

OTHER PUBLICATIONS

The Free Dictionary by Farlex, "anchor," https://www.thefreedictionary.com/anchor.*

(Continued)

*Primary Examiner* — Victoria Hicks Fisher
(74) *Attorney, Agent, or Firm* — Young Basile Hanlon & MacFarlane, P.C.

(57) ABSTRACT

A dental appliance for treating sleep apnea is disclosed. The appliance may include upper and lower portions and at least one biasing member. The upper portion may include a first base and a first feature. The first base may engage the upper teeth of a patient. The first feature may secure to an anterior area of the first base and include a concave surface forming a concavity. The lower portion may include a second base and a second feature. The second base may engage the lower teeth of the patient. The second feature may secure to an anterior area of the second base and include a protrusion. As the patient bites down, the protrusion may contact the concave surface at a point of contact that is a sole or initial contact between the upper and lower portions. Thus, the interaction of the protrusion and concave surface may control certain mandibular loadings and motions of the patient. The biasing member connect the upper portion to the lower portion and urge the lower portion toward the upper portion and in an anterior direction, which may tend to open an airway of the patient.

20 Claims, 19 Drawing Sheets

Related U.S. Application Data filed on Nov. 8, 2013, provisional application No. 61/841,682, filed on Jul. 1, 2013.

(56) References Cited

U.S. PATENT DOCUMENTS

| | | | |
|---|---|---|---|
| 5,795,150 A | 8/1998 | Boyd | |
| 5,823,193 A * | 10/1998 | Singer | A61F 5/566 128/848 |
| 5,868,138 A * | 2/1999 | Halstrom | A61F 5/566 128/848 |
| 5,947,724 A | 9/1999 | Frantz et al. | |
| 6,109,265 A * | 8/2000 | Frantz | A61F 5/566 128/848 |
| 6,450,167 B1 * | 9/2002 | David | A61C 7/08 128/848 |
| 6,581,603 B1 | 6/2003 | Schames | |
| 6,666,212 B2 | 12/2003 | Boyd, Sr. | |
| 6,983,752 B2 | 1/2006 | Garabadian | |
| 7,178,529 B2 | 2/2007 | Kownacki | |
| 7,607,438 B2 | 10/2009 | Pelerin | |
| 7,654,267 B2 | 2/2010 | Boyd | |
| 8,156,940 B2 | 4/2012 | Lee | |
| 8,166,976 B2 | 5/2012 | Webster et al. | |
| 8,770,196 B2 | 7/2014 | Peake et al. | |
| 8,882,497 B2 | 11/2014 | Frantz et al. | |
| 2004/0007239 A1 | 1/2004 | Eubank | |
| 2004/0177852 A1 * | 9/2004 | Abramson | A61F 5/566 128/848 |
| 2004/0177853 A1 * | 9/2004 | Kownacki | A61F 5/566 128/848 |
| 2005/0072435 A1 | 4/2005 | Eubank | |
| 2006/0174897 A1 * | 8/2006 | Sarkisian | A61F 5/566 128/859 |
| 2007/0125388 A1 | 6/2007 | Thornton et al. | |
| 2007/0283967 A1 | 12/2007 | Bailey | |
| 2008/0000483 A1 | 1/2008 | Halstrom | |
| 2008/0199824 A1 * | 8/2008 | Hargadon | A61F 5/566 433/6 |
| 2009/0032030 A1 | 2/2009 | Callender | |
| 2009/0308401 A1 * | 12/2009 | Orrico | A61F 5/566 128/848 |
| 2010/0307511 A1 | 12/2010 | Meade | |
| 2011/0195376 A1 | 8/2011 | Boyd, Sr. | |
| 2011/0277774 A1 * | 11/2011 | Connell | A61F 5/566 128/848 |
| 2011/0308531 A1 * | 12/2011 | Grosky | A61F 5/566 128/848 |
| 2013/0014765 A1 | 1/2013 | Meade | |
| 2014/0060549 A1 * | 3/2014 | Lucas | A61C 7/36 128/861 |
| 2015/0007830 A1 * | 1/2015 | Remmers | A61F 5/566 128/848 |
| 2015/0216716 A1 | 8/2015 | Anitua Aldecoa | |

OTHER PUBLICATIONS

BruxSplint, www.chairsidesplint.com, pp. 1-8, accessed May 29, 2013.

Listing of NTI type and BruxSplint Devices, www.chairsidesplint.com, pp. 1-4, accessed May 29, 2013.

Night Guards, www.landmarkdental.net, pp. 1-2, accessed May 29, 2013.

Written Opinion of the International Searching Authority, International Application No. PCT/US2014/045162, Oct. 16, 2014, pp. 1-4.

Translation of ES2542577.

* cited by examiner

DENTAL APPLIANCE FOR TREATMENT OF SLEEP APNEA

RELATED APPLICATIONS

This application (1) claims the benefit of U.S. Provisional Patent Application Ser. No. 62/028,860 filed Jul. 25, 2014 and (2) is a continuation-in-part of U.S. patent application Ser. No. 14/321,648 filed Jul. 1, 2014, which claims the benefit of U.S. Provisional Patent Application Ser. No. 61/841,682 filed Jul. 1, 2013 and U.S. Provisional Patent Application Ser. No. 61/901,696 filed Nov. 8, 2013.

U.S. Provisional Patent Application Ser. No. 62/028,860, U.S. patent application Ser. No. 14/321,648, U.S. Provisional Patent Application Ser. No. 61/841,682, and U.S. Provisional Patent Application Ser. No. 61/901,696 are each hereby incorporated by reference.

BACKGROUND

The Field of the Invention

This invention relates to dental systems and, more particularly, to novel systems and methods for treating sleep apnea.

The Background Art

Sleep apnea is a sleep disorder typically characterized by pauses in breathing. These pauses cause carbon dioxide to build up in the bloodstream. In response to this build-up, the brain wakes the person from sleeping. Once awake, normal breathing may resume and the person may fall asleep again. However, the interruption, or a series of such interruptions may prevent the person from getting adequate rest. This may in turn produce daytime fatigue, a slower reaction time, vision problems, an increased risk of diabetes, and the like. Accordingly, what is needed is an apparatus and method for preventing sleep apnea and the negative consequences thereof.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF SELECTED EMBODIMENTS

Figure 1:
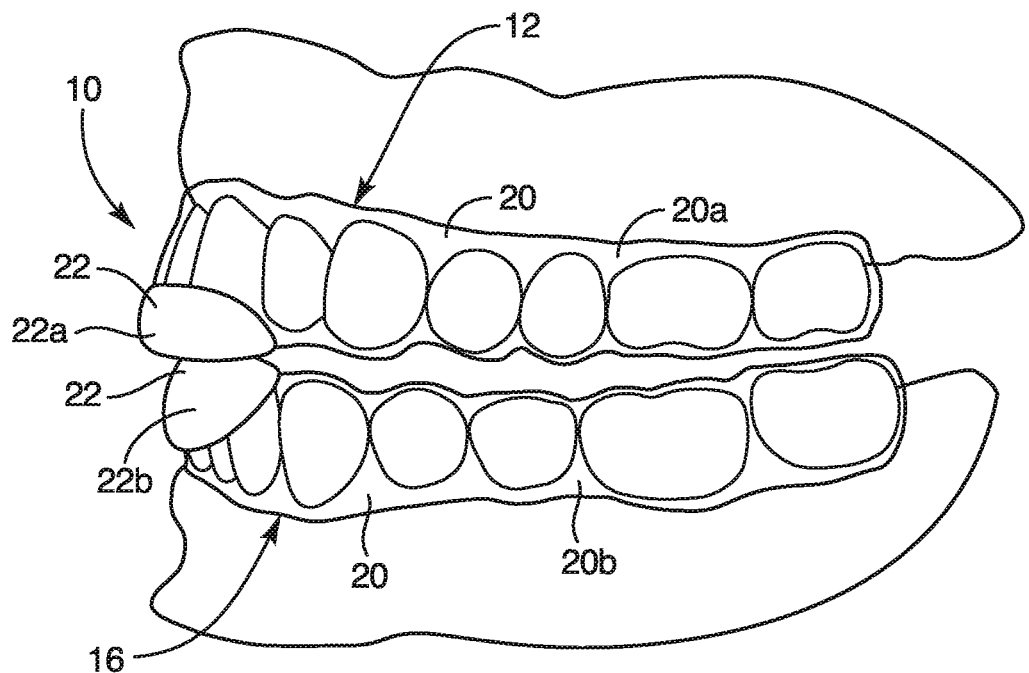
FIG. 1 is a side view of one embodiment of a dental appliance in accordance with the present invention installed on a patient.
Figure 1:
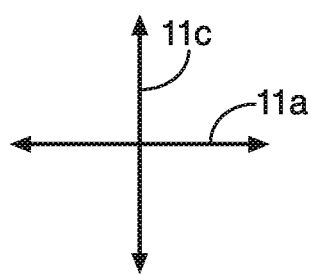

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Figure 2:
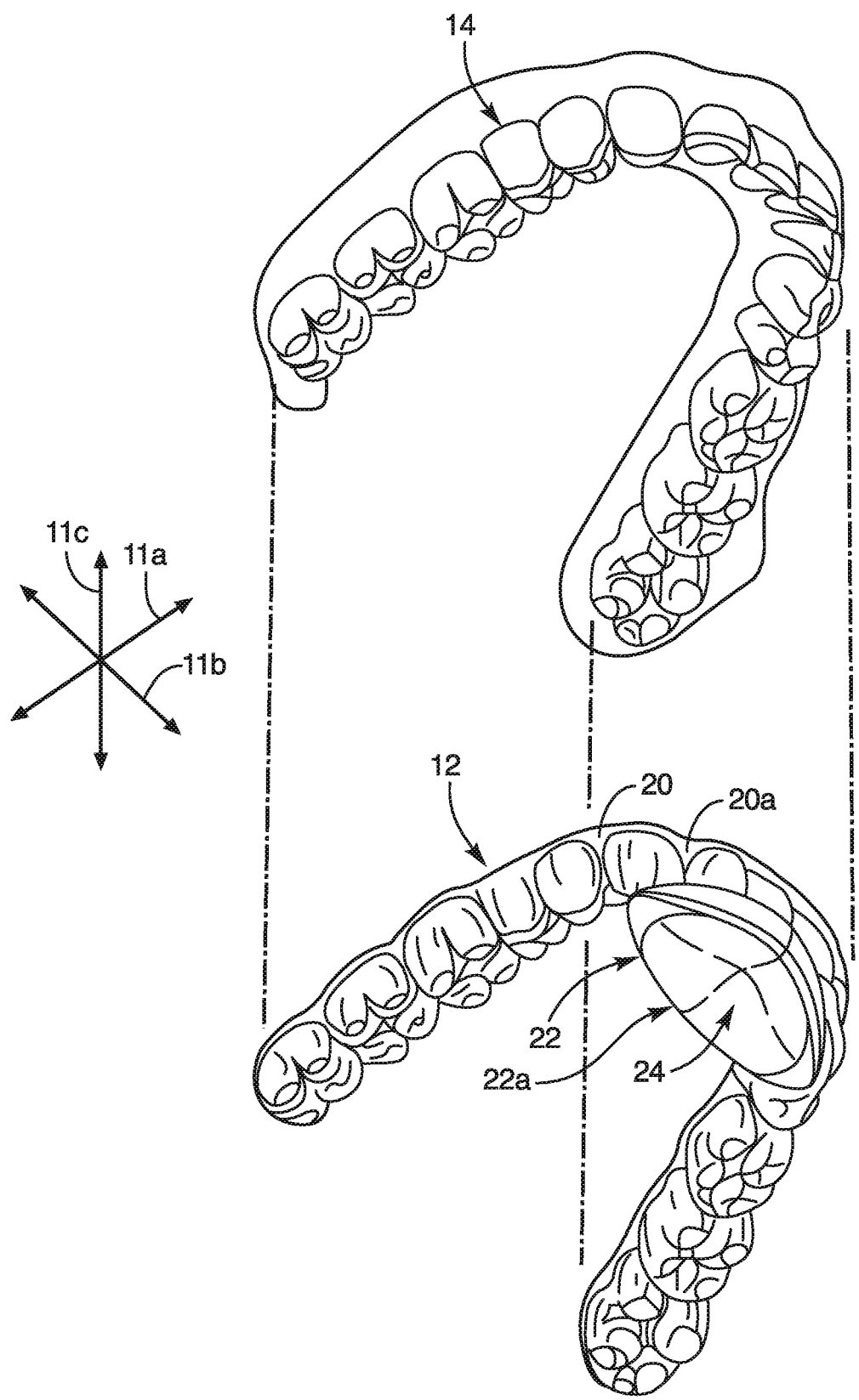
FIG. 2 is a perspective view of one embodiment of an upper portion of a dental appliance in accordance with the present invention.
Figure 3:
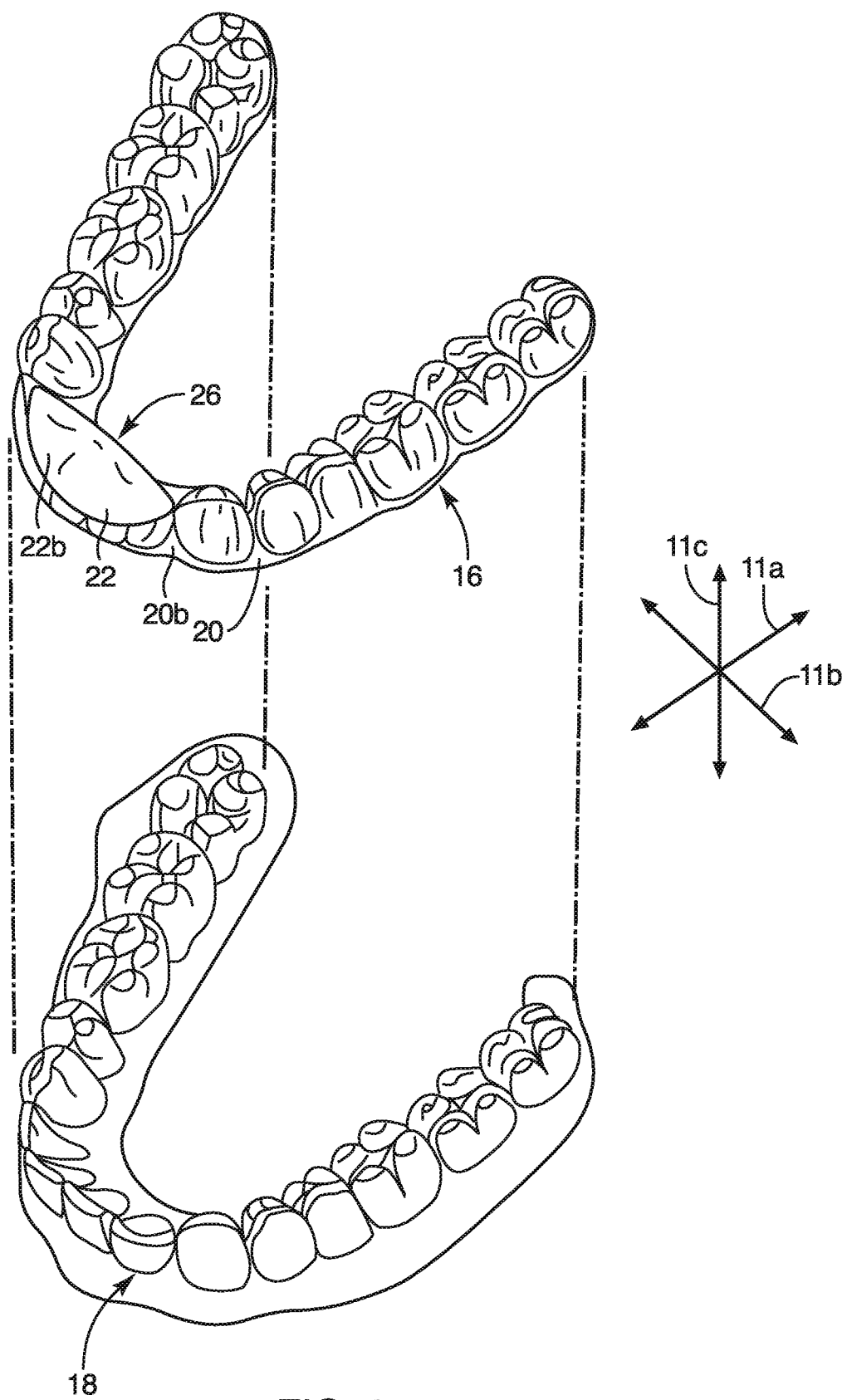
FIG. 3 is a perspective view of one embodiment of a lower portion of a dental appliance in accordance with the present invention.
Figure 4:
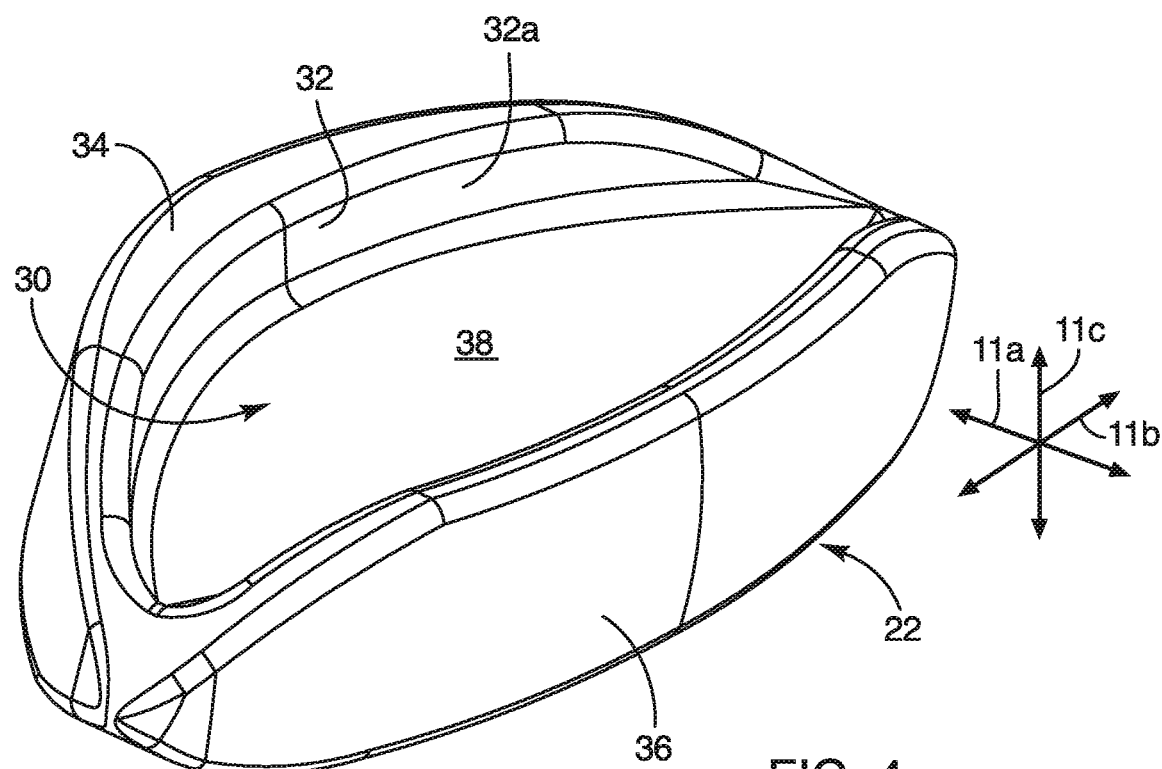
FIG. 4 is a perspective view of one embodiment of a feature having an indentation or recess in accordance with the present invention.
Figure 5:
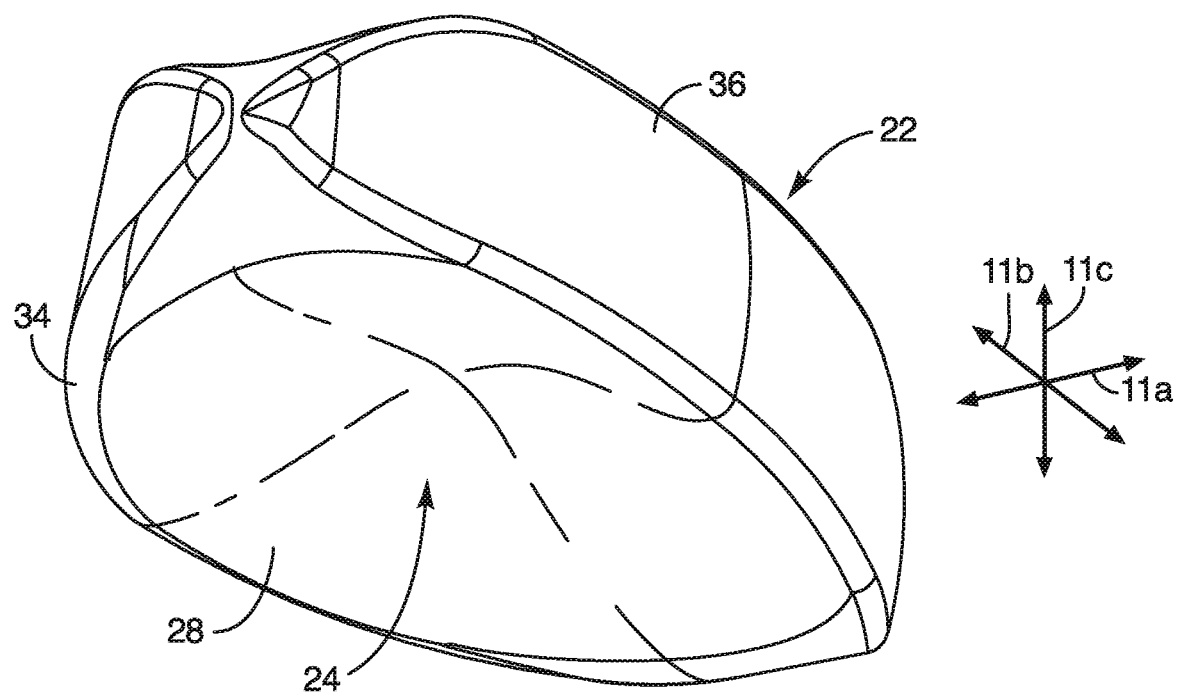
FIG. 5 is another perspective view of the feature of FIG. 4.
Figure 6:
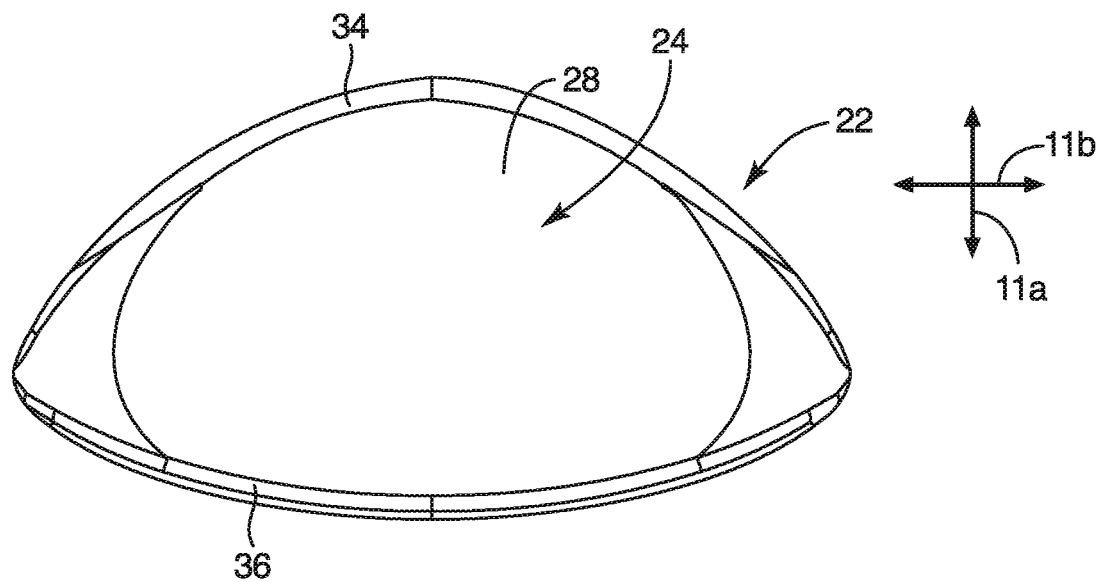
FIG. 6 is a bottom view of the feature of FIG. 4.
Figure 7:
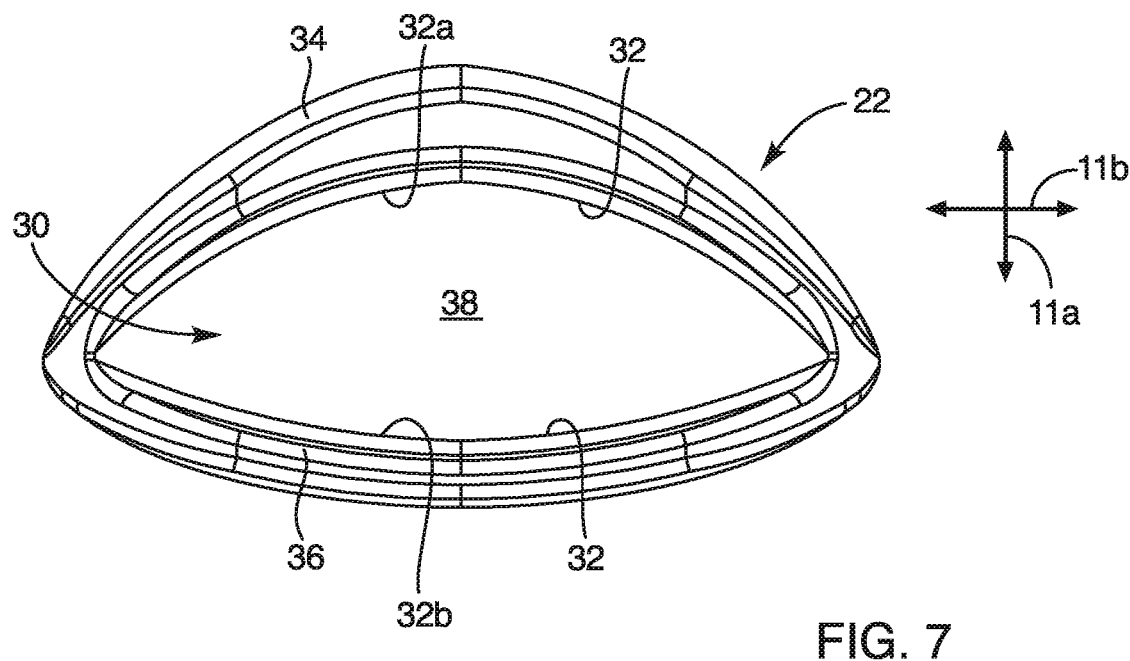
FIG. 7 is a top view of the feature of FIG. 4.
Figures 8, 9:
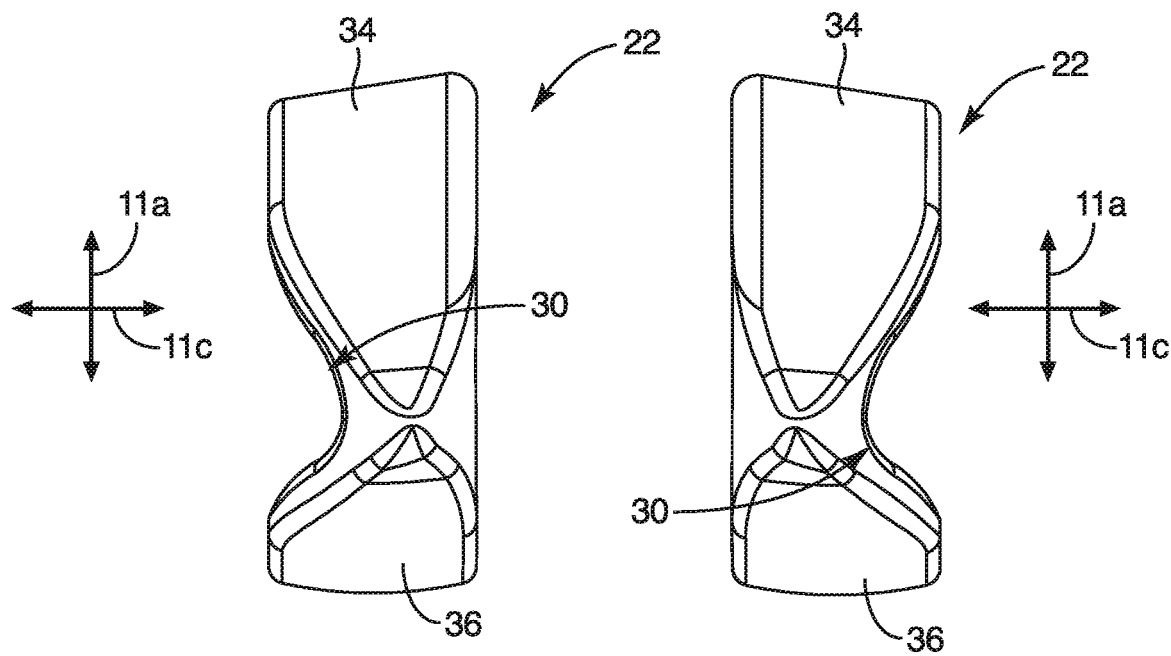
FIG. 8 is a first side view of the feature of FIG. 4.
FIG. 9 is a second, opposite side view of the feature of FIG. 4.
Figure 10:
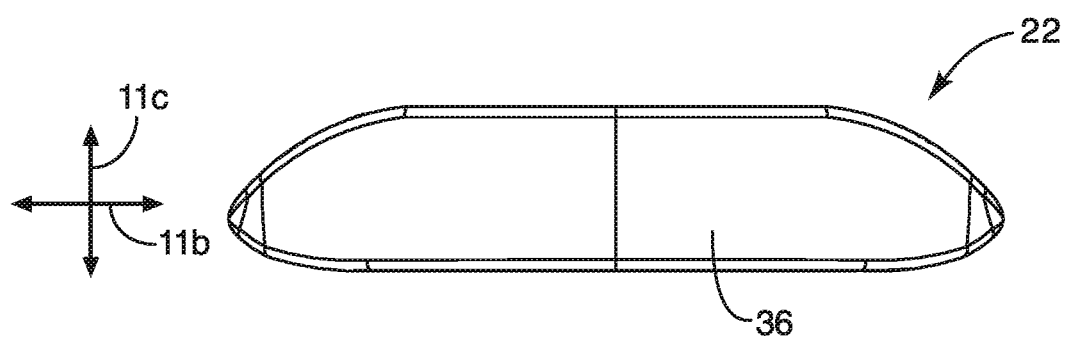
FIG. 10 is a rear view of the feature of FIG. 4.
Figure 11:
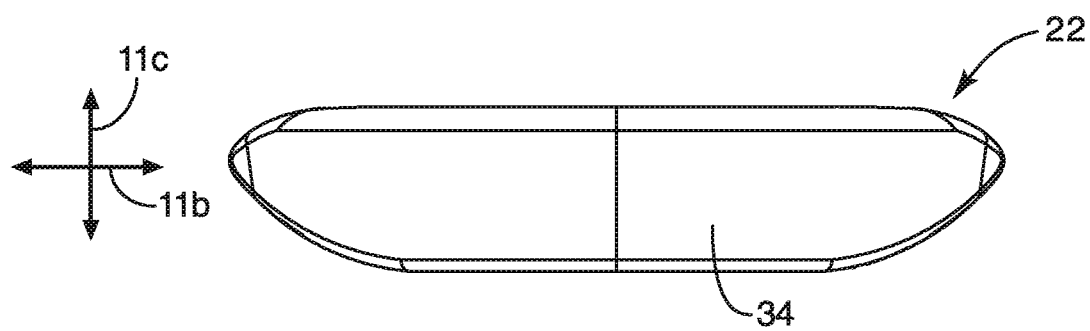
FIG. 11 is a front view of the feature of FIG. 4.
Figure 12:
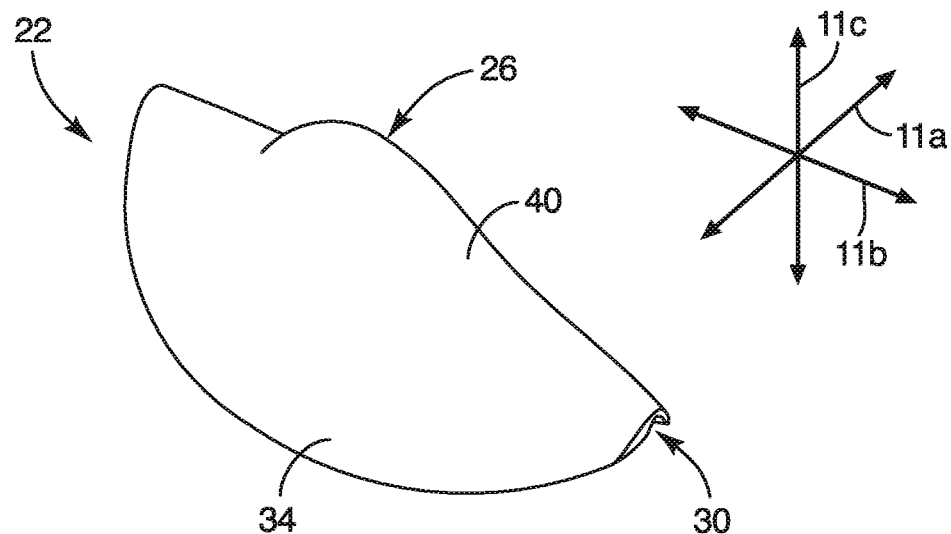
FIG. 12 is a perspective view of one embodiment of a feature having a protrusion or mound in accordance with the present invention.
Figure 13:
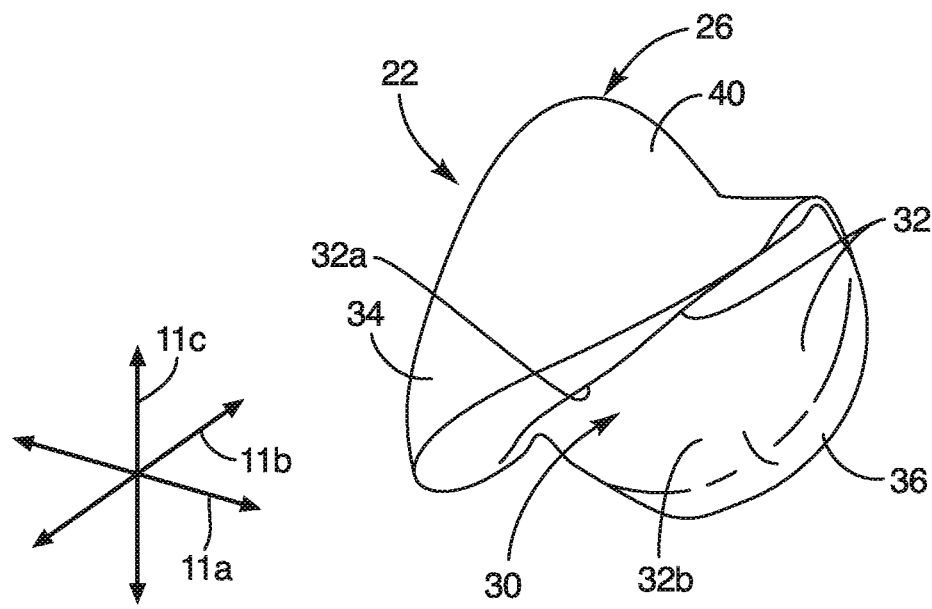
FIG. 13 is another perspective view of the feature of FIG. 12.
Figure 14:
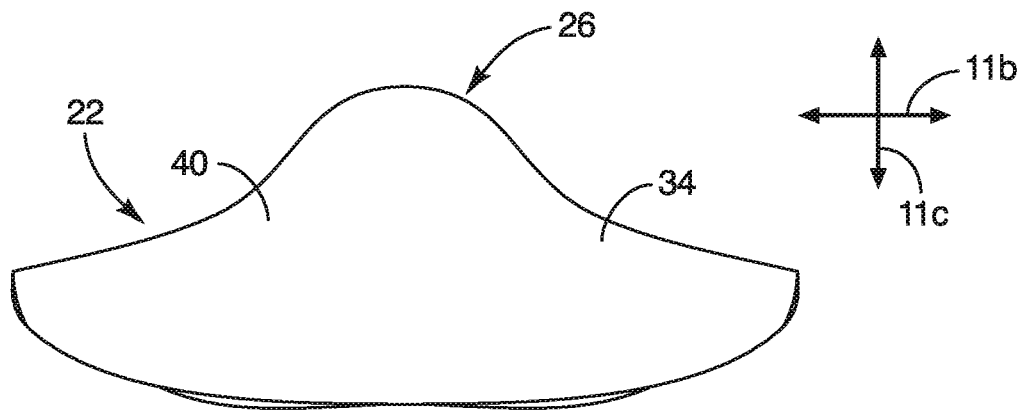
FIG. 14 is a front view of the feature of FIG. 12.
Figure 15:
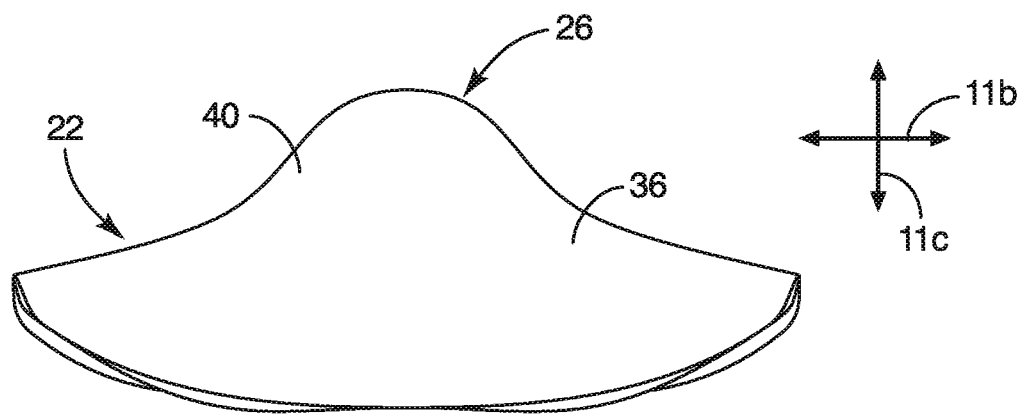
FIG. 15 is a back view of the feature of FIG. 12.
Figure 16:
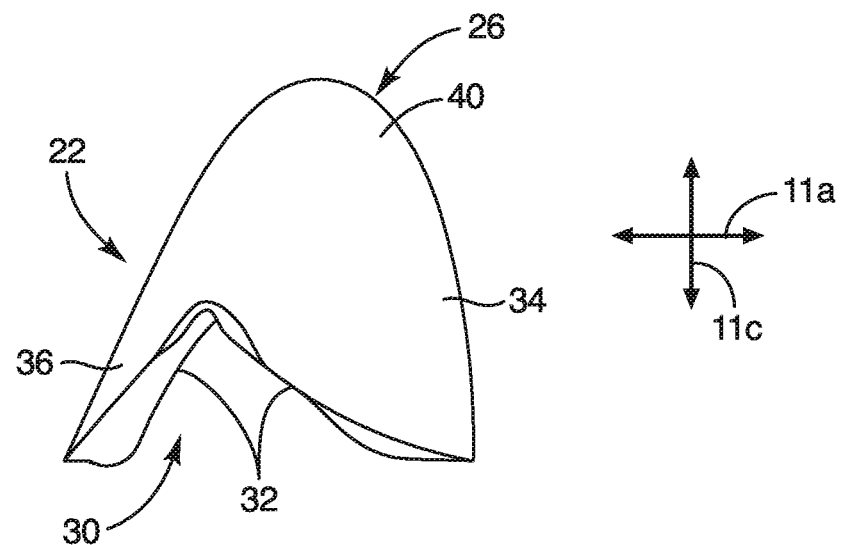
FIG. 16 is a first side view of the feature of FIG. 12.
Figure 17:
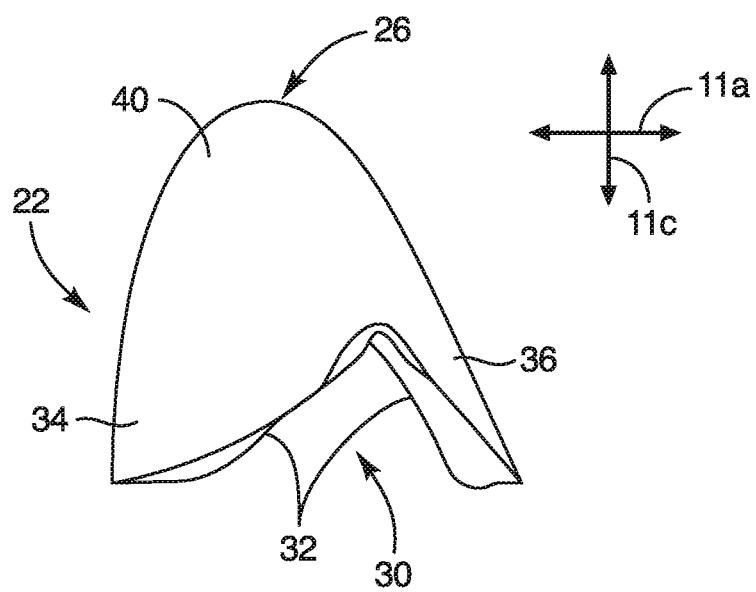
FIG. 17 is a second, opposite side view of the feature of FIG. 12.
Figure 18:
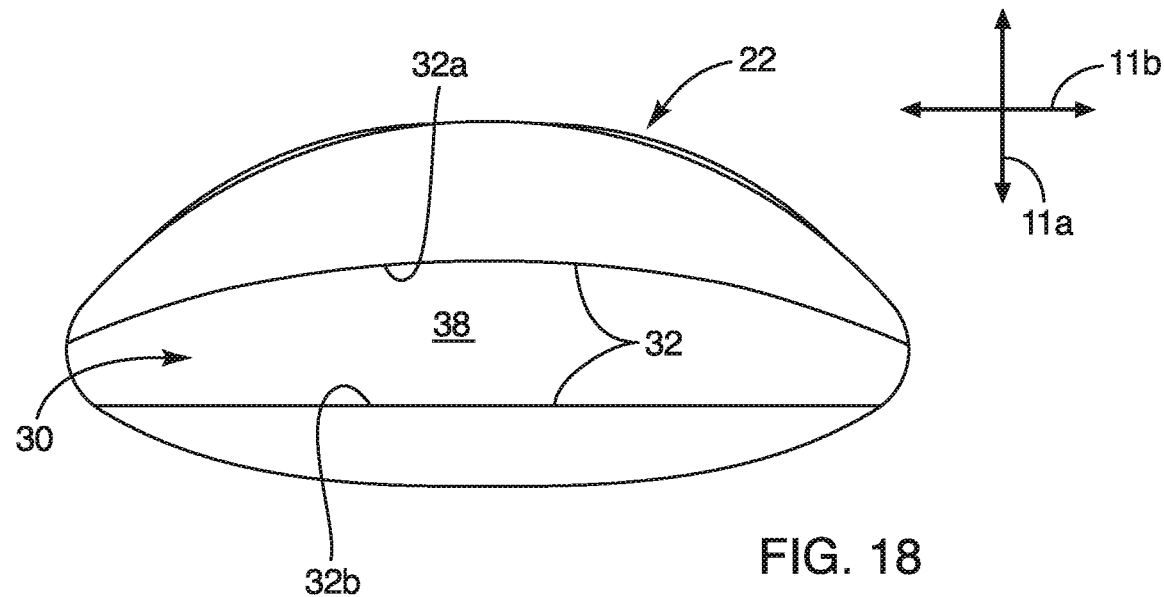
FIG. 18 is a bottom view of the feature of FIG. 12.
Figure 19:
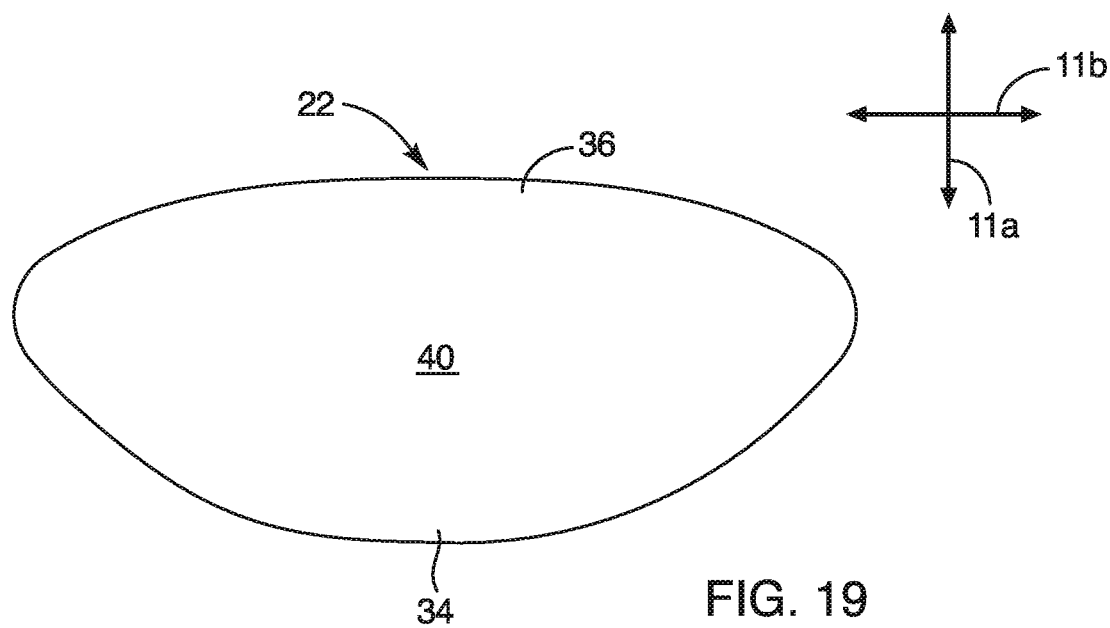
FIG. 19 is a top view of the feature of FIG. 12.
Figure 20:
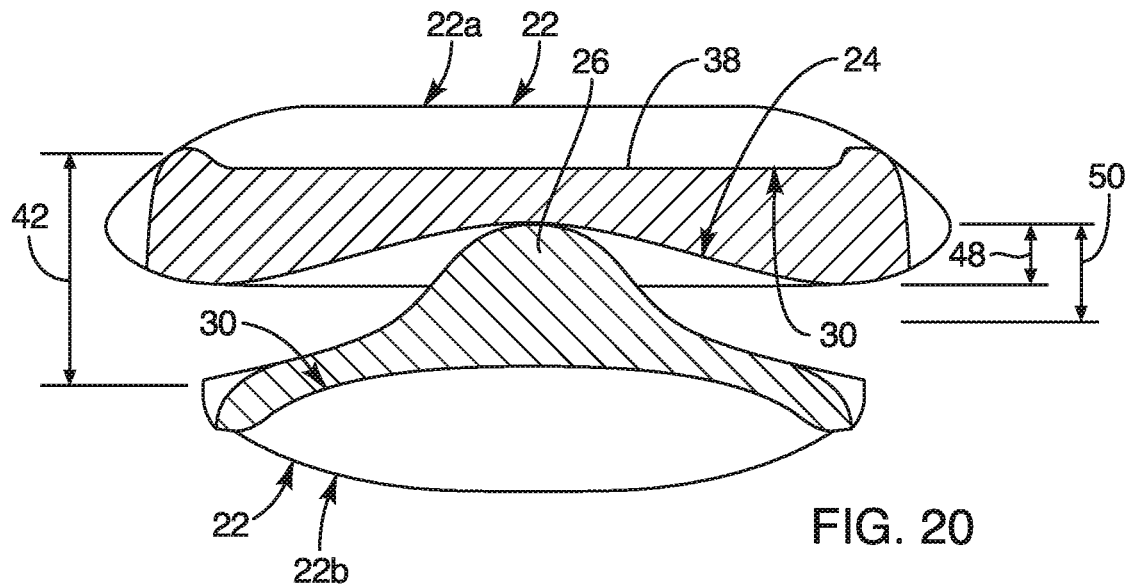
FIG. 20 is a partial, cross-sectional, front view of one embodiment of a dental appliance wherein the feature of FIG. 4 and the feature of FIG. 12 are abutting and aligned in accordance with the present invention.
Figure 21:
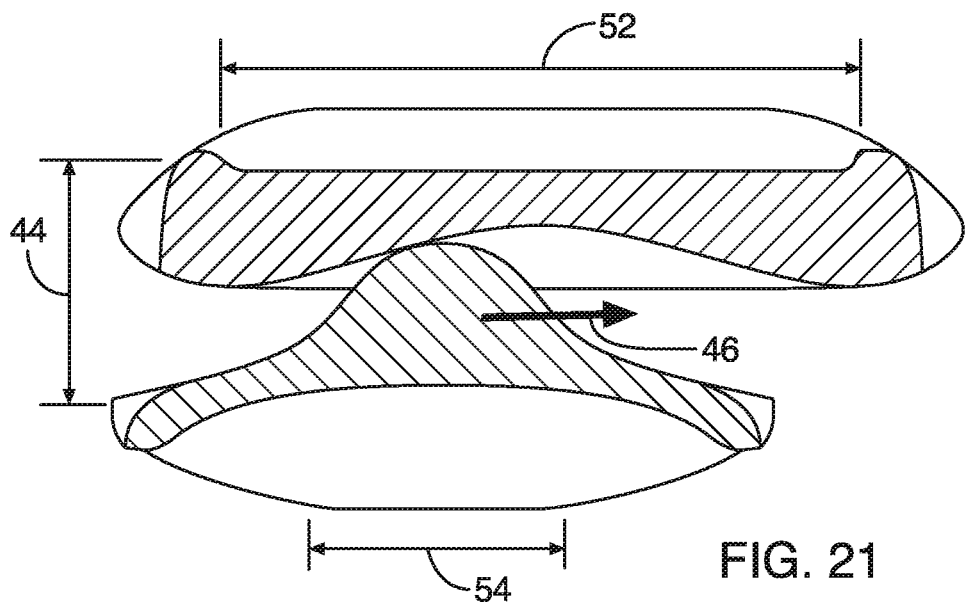
FIG. 21 is a partial, cross-sectional, front view the dental appliance of FIG. 20 wherein the feature of FIG. 4 and the feature of FIG. 12 are abutting and the feature of FIG. 12 is shifted to the left in accordance with the present invention.
Figure 22:
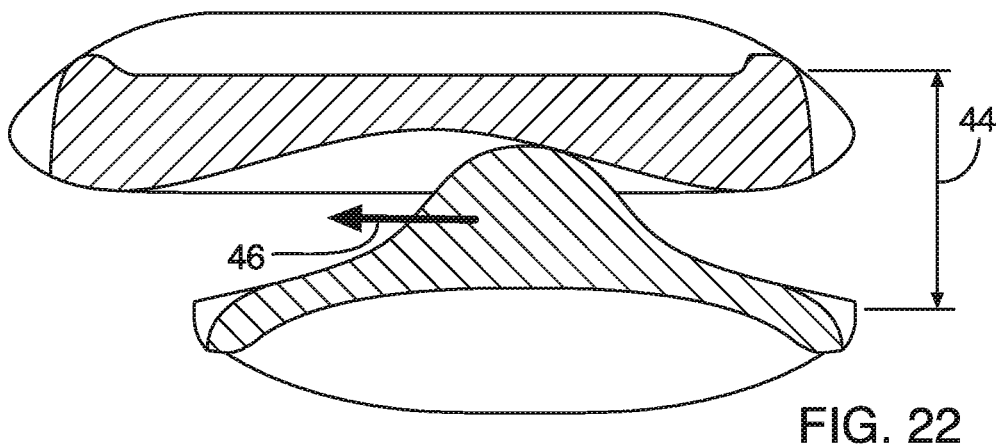
FIG. 22 is a partial, cross-sectional, front view the dental appliance of FIG. 20 wherein the feature of FIG. 4 and the feature of FIG. 12 are abutting and the feature of FIG. 12 is shifted to the right in accordance with the present invention.
Figure 23:
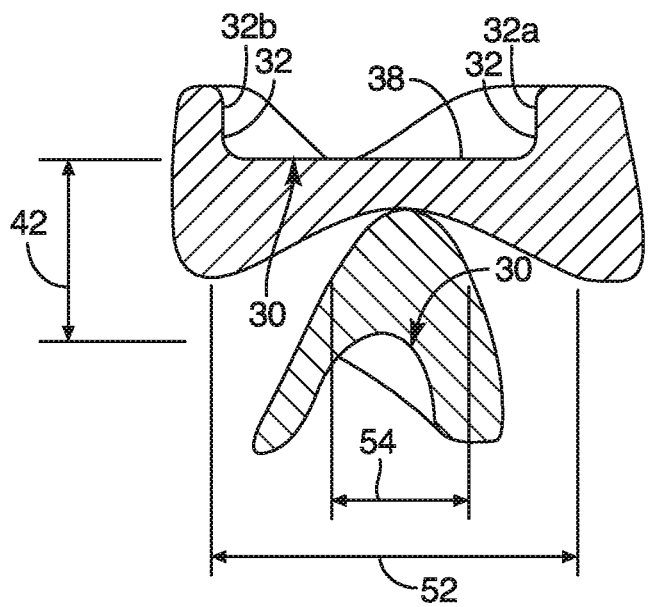
FIG. 23 is a partial, cross-sectional, side view on one embodiment of a dental appliance wherein the feature of FIG. 4 and the feature of FIG. 12 are abutting and aligned in accordance with the present invention.
Figure 24:
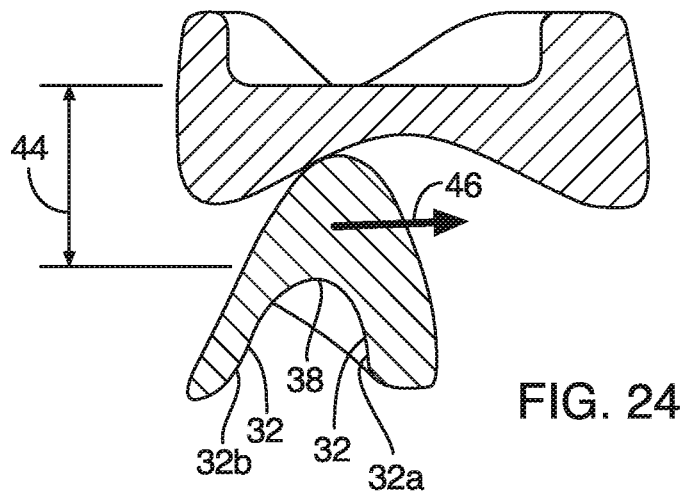
FIG. 24 is a partial, cross-sectional, side view the dental appliance of FIG. 23 wherein the feature of FIG. 4 and the feature of FIG. 12 are abutting and the feature of FIG. 12 is shifted rearward in accordance with the present invention.
Figure 25:
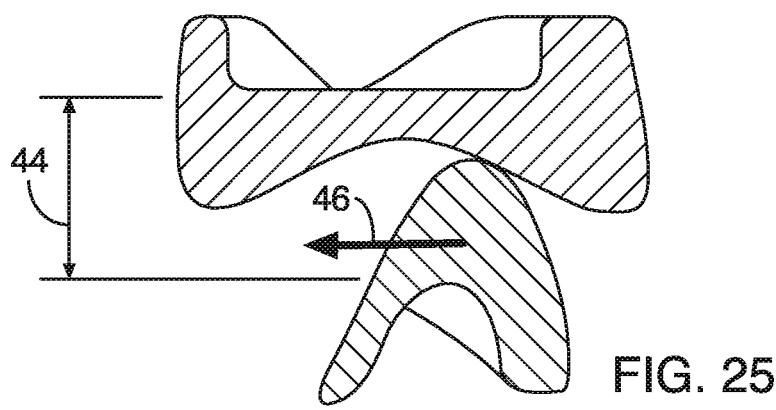
FIG. 25 is a partial, cross-sectional, side view the dental appliance of FIG. 23 wherein the feature of FIG. 4 and the feature of FIG. 12 are abutting and the feature of FIG. 12 is shifted forward in accordance with the present invention.
Figure 26:
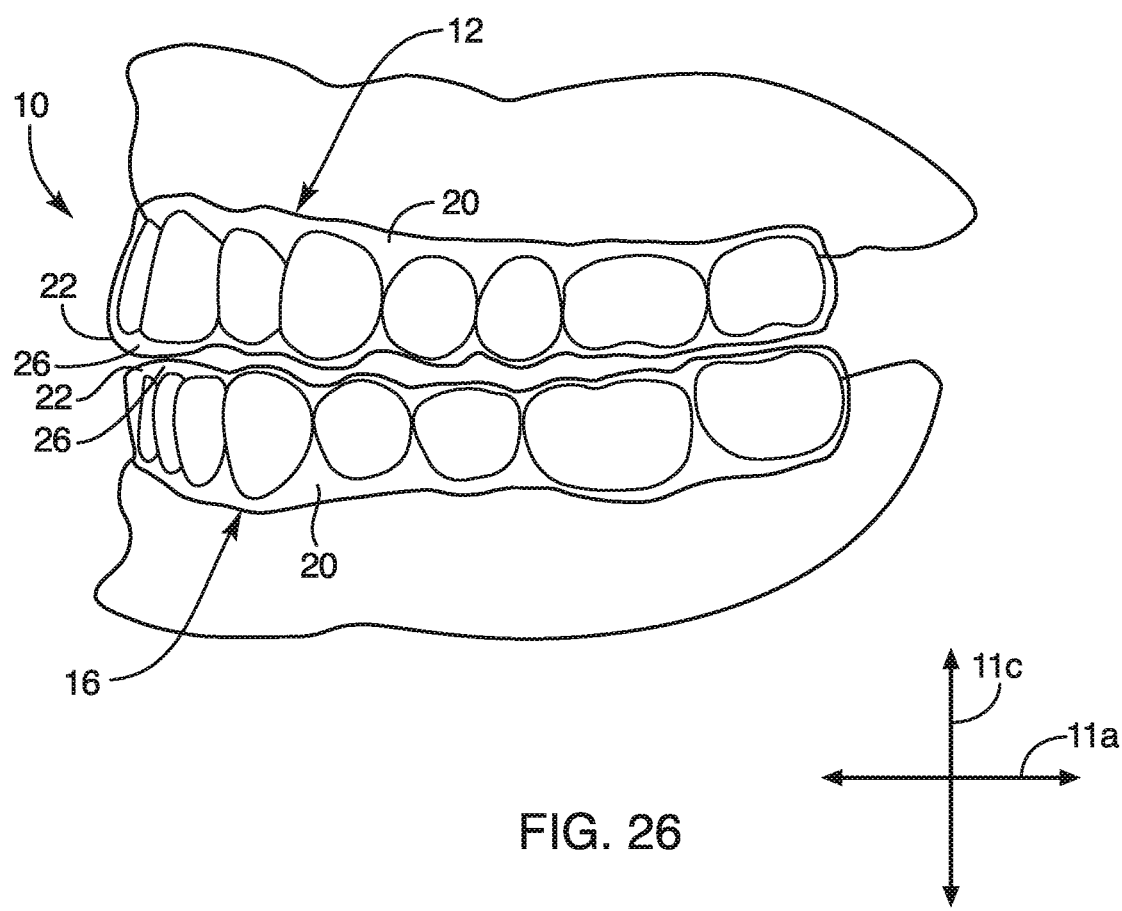
FIG. 26 is a side elevation view of an alternative embodiment of a dental appliance in accordance with the present invention installed on a patient.
Figure 27:
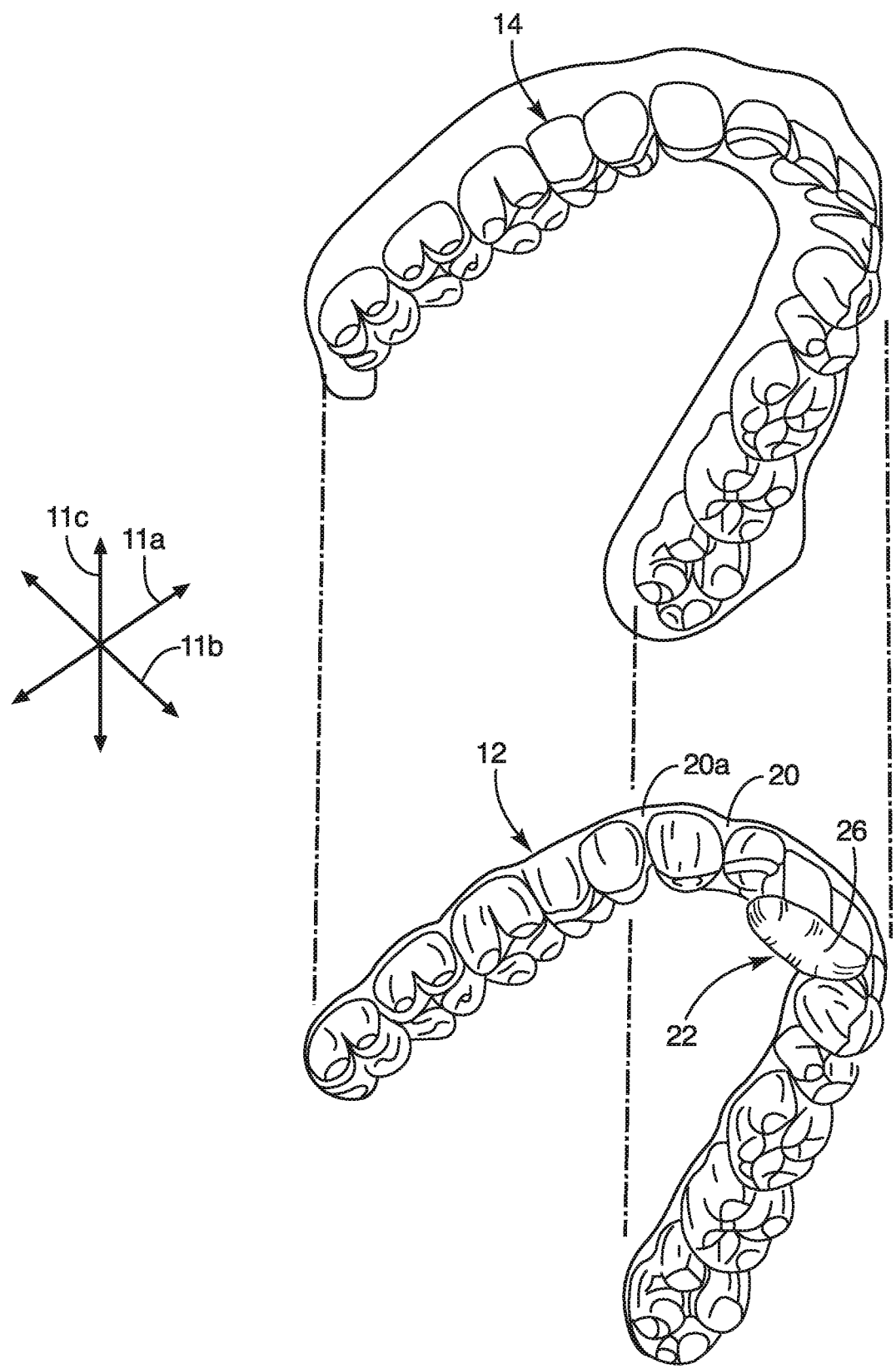
FIG. 27 is a perspective view of an alternative embodiment of an upper portion of a dental appliance in accordance with the present invention.
Figure 28:
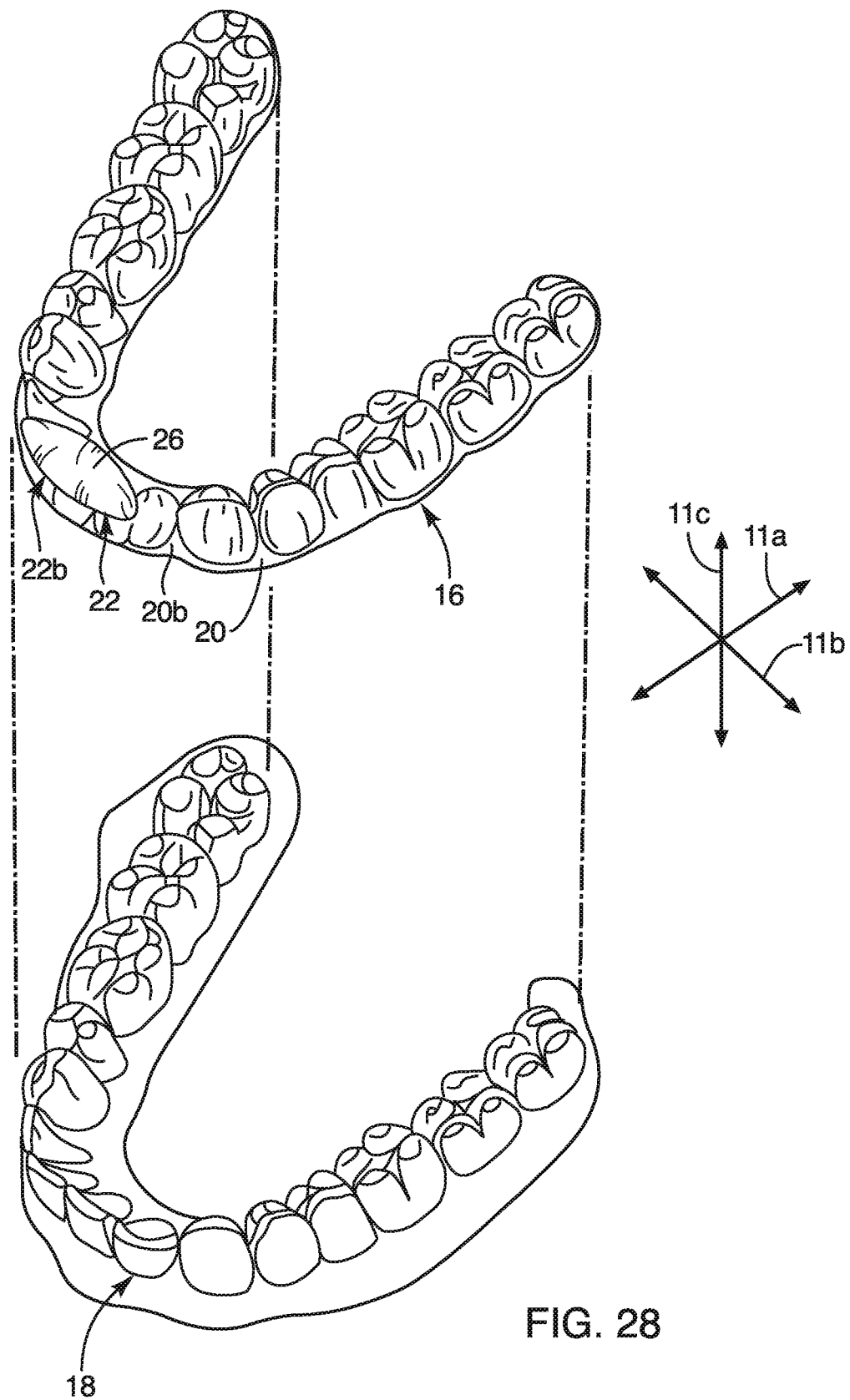
FIG. 28 is a perspective view of an alternative of a lower portion of a dental appliance in accordance with the present invention.
Figure 29:
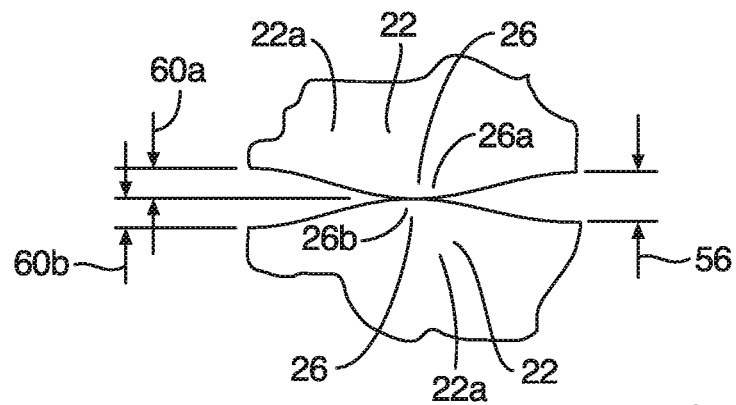
FIG. 29 is a partial front view of one embodiment of a dental appliance wherein opposing protrusions of the upper and lower portions are abutting and aligned in accordance with the present invention.
Figure 30:
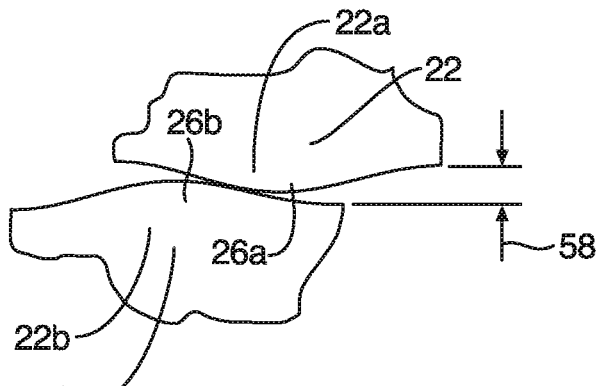
FIG. 30 is a partial front elevation view the dental appliance of FIG. 29 wherein the upper and lower portions are abutting and the lower portion is shifted to the left in accordance with the present invention.
Figure 31:
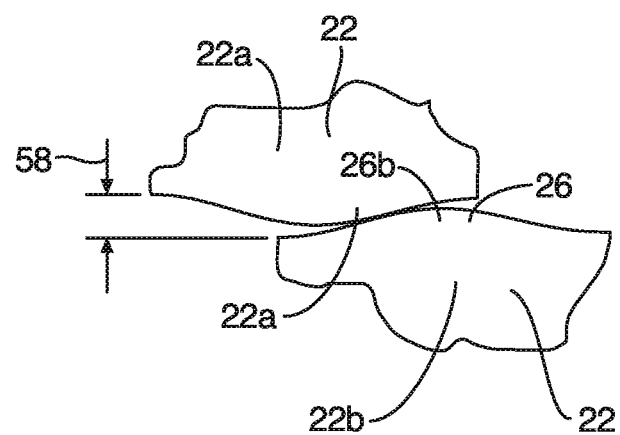
FIG. 31 is a partial front elevation view the dental appliance of FIG. 29 wherein the upper and lower portions are abutting and the lower portion is shifted to the right in accordance with the present invention.
Figure 32:
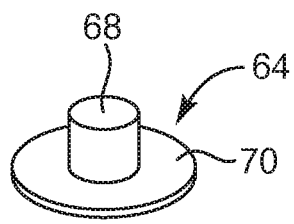
FIG. 32 is a perspective view of one embodiment of an engagement mechanism in accordance with the present invention.
Figure 33:
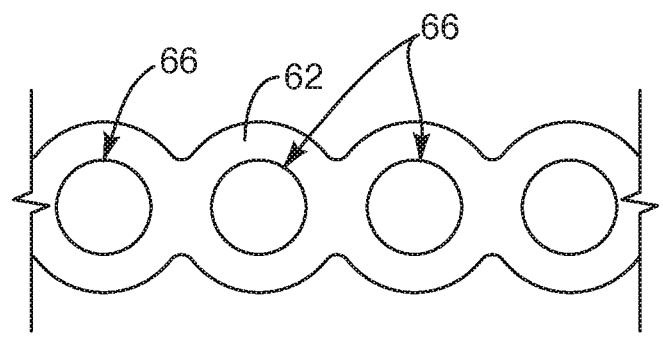
FIG. 33 is a side view of a portion of one embodiment of a biasing member in accordance with the present invention.
Figure 34:
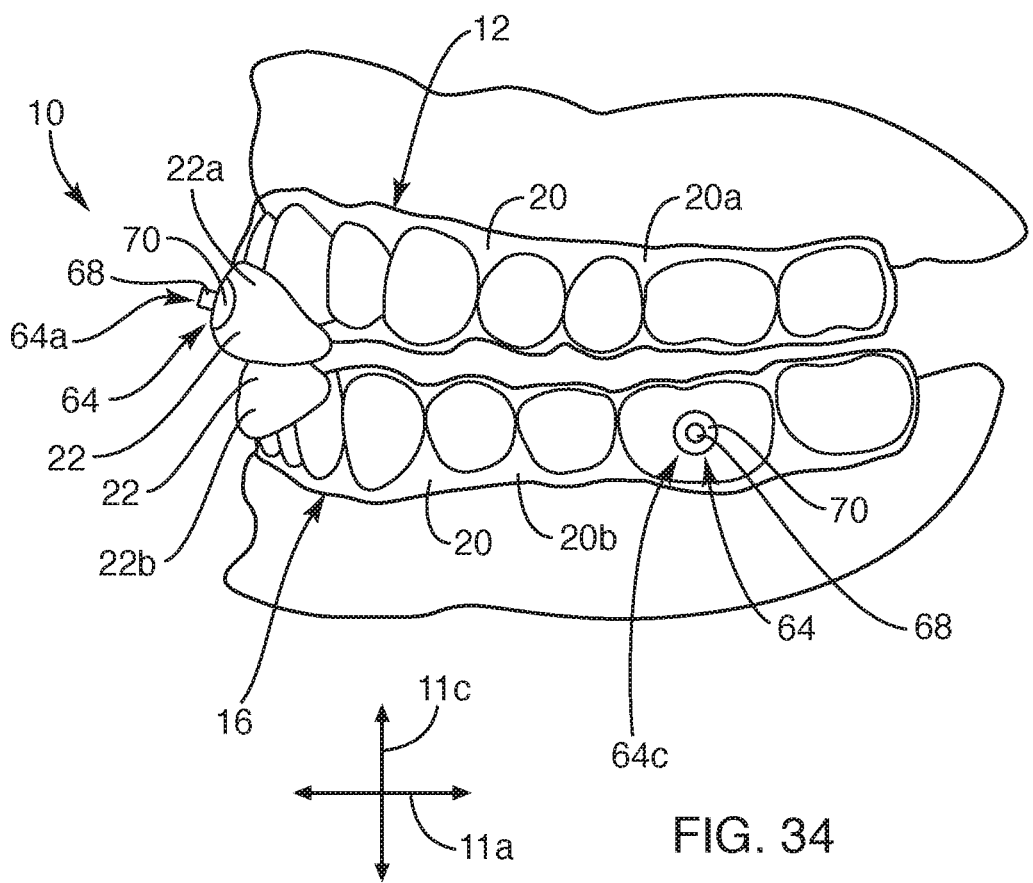
FIG. 34 is a side view of an alternative embodiment of a dental appliance in accordance with the present invention installed on a patient.

Referring to FIGS. 1-3, bruxism may cause unnecessary muscle strain, tension, and pain. For example, while grinding and clenching teeth, jaw muscles may be contracted and strained for extended periods of time. Additionally, grinding and clenching of teeth may cause muscle strain and tension in other areas. For example, bruxism may produce muscle strain, tension, and pain in the muscles of the neck. Bruxism may cause sleep problems as well.

For example, when the muscular systems of the head and neck are contracting, a patient may not enter deeper levels of sleep. Thus, habitual clenching and grinding can prevent the parasympathetic system from operating at its potential. A depressed immune system, lower metabolism, depressed neurotransmitter activity, lower reaction time, high stress levels, feelings of depression and more have all been documented and linked to lack of deep sleep.

Additionally, muscle tension and stress from over worked muscles and lack of sleep are a leading cause of headaches. When the brain receives too much bad sensory information, it may translate to a headache. The motor component of the trigeminal nerve can send a lot of bad sensory information to the brain. Thus, headaches may be a symptom of bruxism.

By treating bruxism, an appliance 10 in accordance with the present invention may cure a host of ailments. For example, an appliance 10 may protect teeth from harmful abrasion and unnecessary wear. An appliance 10 may also reduce inflammation of the periodontal ligament (PDL), reduce pulpitis of the teeth, preserve an orthodontic tooth position, reduce muscle strain, tension, and pain in the muscles of the jaw, reduce muscle strain, tension, and pain in the muscles of the neck, enable a user to enter deeper levels of sleep, and/or reduce head aches.

In describing an appliance 10 in accordance with the present invention, it may be helpful to define a coordinate system. For example, in selected embodiments, an appliance 10 may be described in terms of a longitudinal direction 11a, lateral direction 11b, and transverse direction 11c. The longitudinal, lateral, and transverse directions 11a, 11b, 11c may extend orthogonally with respect to one another.

In selected embodiments, an appliance 10 in accordance with the present invention may include an upper portion 12 corresponding to (e.g., engaging, covering, being worn over) one or more maxillary teeth 14 (upper teeth) of a patient and a lower portion 16 corresponding to (e.g., engaging, covering, being worn over) one or more mandibular teeth 18 (lower teeth) of the patient. In certain embodiments, a method may include obtaining an appliance 10 and applying the appliance 10 so that the upper and lower portions 12, 16 of the appliance 10 may be worn simultaneously.

An appliance 10 may cover all of the teeth of a patient or some subset thereof. For example, in selected embodiments, an upper portion 12 may engage or cover all or substantially all maxillary teeth 14 of a patient and a lower portion 16 may engage or cover all or substantially all mandibular teeth 18 of the patient. This may allow for orthodontic retention, product delivery (e.g., application of a whitening product to the teeth), or the like or a combination thereof. Alternatively, one or both of an upper portion 12 and a lower portion 16 may respectively cover less than (e.g., substantially less than) all of the maxillary and mandibular teeth of a patient.

In selected embodiments, upper and lower portions 12, 16 in accordance with the present invention may each include a base 20 and a feature 22. For example, an upper portion 12 may include a first base 20a and a first feature 22a, while a lower portion 16 may include a second base 20b and a second feature 22b.

A base 20 may be shaped to selectively engage one or more teeth of a patient. A feature 22 may be secured to a base 20. Thus, a base 20 may interface between a feature 22 and certain teeth of a patient. For example, a base 20 may be custom made to closely fit certain teeth of a patient. Accordingly, when the base 20 is applied to the one or more teeth, the base 20 may tend to stay there by mechanical gripping, suction, or the like or some combination thereof. Thus, once a base 20 is applied to one or more teeth, a corresponding feature 20 may be held in a desired orientation or position with respect to the teeth. However, the base 20 and corresponding feature 22 may be removed from the patient by simply pulling the base 20 away from the corresponding teeth.

In certain embodiments, an appliance 10 may include features 22 positioned opposite one another. For example, a first feature 22a of an upper portion 12 may be positioned opposite a second feature 22b of a lower portion 16. Accordingly, mandibular motion of a patient (e.g., biting down) may result in a first feature 22a contacting a second feature 22b.

In selected embodiments, features 22 may be positioned and shaped to interface or interact with one another in a particular manner. For example, a first feature 22a may comprise an indentation 24 or recess 24 and a second feature 22b may comprise a protrusion 26 or mound 26. Alternatively, a first feature 22a may comprise a protrusion 26 or mound 24 and a second feature 22b may comprise an indentation 24 or recess 24. Thus, while FIGS. 1-3 show an indentation 24 forming part of an upper portion 12 and a protrusion 26 forming part of a lower portion 16, in other embodiments, a protrusion 26 may form part of an upper portion 12 and an indentation 24 may form part of a lower portion 16.

In certain embodiments, features 22 may be positioned and shaped to interface or interact with one another to control, direct, or influence the mandibular motion, mandibular loadings, or the like of a corresponding patient. For example, when an appliance 10 is in place, opposing first and second features 22a, 22b may be located on or secured to anterior areas of the respective first and second bases 20a, 20b. Moreover, the first and second features 22a, 22b may be shaped, sized, or position such that contact therebetween may be or comprise an initial, primary, or exclusive point of contact for forces of occlusion (e.g., biting loads) or the like passing (transferring) form mandibular teeth to maxillary teeth of the corresponding patient (e.g., a majority of a force associated with biting may be transferred through the point of contact).

As a result, an appliance 10 may cause all forces of occlusion to be directed to the front of the mouth or to the front teeth (e.g., maxillary central incisors, maxillary lateral incisors, mandibular central incisors, mandibular lateral incisors, or the like or combinations or sub-combinations thereof). The brain of a patient may not allow the muscles of mastication to produce the same force of occlusion when pressure is only on the front teeth. That is, an appliance 10 may not allow the muscles around the joint to contract at full strength. Thus, an appliance may 10 may prevent a patient from clenching or grinding teeth and provide to the patient the benefits associated therewith.

An appliance 10 in accordance with the present invention may be manufactured in any suitable manner. In selected embodiments, a base 20 and corresponding feature 22 may be made as a monolithic unit by three-dimensional printing, photo-activation, machining, casting, molding, or the like. Alternatively, impressions (e.g., actual or digital impressions) of a patient's teeth may be taken and models of the patient's teeth may be fabricated. Polymeric material (e.g., acrylic sheets) may be applied to and/or formed around the modeled teeth to form first and second bases 20a, 20b. Thus, the bases 20 may be custom made to closely fit (follow contours of) selected teeth of a patient. Once the bases 20 are formed, appropriate features 22 may be applied thereto.

Features 22 in accordance with the present invention may be manufactured from any suitable material or combinations of materials. Suitable materials may include polymers, ceramics, metals, metal alloys, or the like. In certain embodiments, features 22 be manufactured as separate, standardized pieces. That is, while a base 20 may be custom made to fit only one patient, a feature 22 may be an "off-the-shelf" item that may be applied to various bases 20. For example, features 22 may be manufactured in one size or in a relative small set of sizes (e.g., small, medium, large, etc.). Then, once a base 20 has been made, an appropriate feature 22 may be selected, positioned, and bonded to an anterior area of the base 20. Alternatively, a feature 22 may be formed by hand from a polymeric material, epoxy, or the like that is molten, in a softened condition, uncured, or the like and urged against or otherwise bonded to a base 20.

In selected embodiments, a feature 22a corresponding to an upper portion 12 may be positioned differently than a feature 22b corresponding to a lower portion 16. This difference may ensure that the two features 22a, 22b properly align when a lower jaw of the corresponding patient is in a desired position (e.g., a neutral, central, forward, lower, or mouth-slightly-open position, or a combination or sub-combination thereof). This desired position may be selected to control jaw position and postural muscles of the neck and head to open the airway of the patient, thereby decreasing snoring and reducing (relieving) the incidence or symptoms of sleep apnea. For example, in certain embodiments, a feature 22a corresponding to an upper portion 12 may be positioned primarily or largely posterior and/or inferior to the maxillary central incisors (e.g. positioned posterior to maxillary central incisors), while a feature 22b corresponding to a lower portion 16 may be positioned primarily or largely superior (and possible anterior or posterior to) the mandibular central incisors (e.g., positioned superior to mandibular central incisors).

Referring to FIGS. 4-11, a feature 22 providing or comprising an indentation 24 or recess 24 may have any suitable configuration. In selected embodiments, such a feature 22 may include a first side having a concave surface 28 forming a concavity, which concavity may be the indentation 24 or recess 24. The feature 22 may also include a second side having a channel 30 facilitating securement of the feature 22 to a base 20.

For example, a channel 30 may provide a location for bonding material to be applied to a feature 22 before the feature 22 is applied to a corresponding base 20. Alternatively, or in addition thereto, in selected embodiments, an aperture 30 or channel 30 may include one or more curved surfaces 32 that track or loosely follow a typical curve associated with an anterior area of a base 20. That is, as a base 20 may curve to accommodate the natural positioning of the incisors, cuspids, bicuspids, etc. of the patient, so a channel 30 or curved surface 32 thereof may curve to accommodate the shape of the base 20. Accordingly, the curved surface 32 may facilitate positioning and stabilizing of a feature 22 with respect to a corresponding base 20.

In selected embodiments, a channel 30 may divide a feature 22 into an anterior portion 34 and a posterior portion 36. When connected to a base 20 and applied to a patient, an anterior portion 34 may be largely or exclusively position anterior to the teeth (e.g., incisors, cuspids, etc.) of the patient. Conversely, a posterior portion 36 may be positioned largely or exclusively posterior to those teeth.

In selected embodiments, one curved surface 32a or side of a channel 30 may be part of an anterior portion 34, while another, opposite curved surface 32b or side of the channel 30 may be part of a posterior portion 36. A channel 30 may have any suitable width in the longitudinal direction 11a between such opposing surfaces 32a, 32b. In selected embodiments, a channel 30 may have a width just wide enough to accommodate the outer or exposed portions of the incisors (or the incisors and cuspids) and the thickness of the base 20 extending thereover. Alternatively, a channel 30 may have a width that significantly wider than the teeth corresponding thereto.

For example, a channel 30 may have one curved surface 32a that tracks or loosely follows the curvature of the anterior side of the teeth, while an opposing curved surface 32b extends posteriorly away from a posterior side of the teeth. In such embodiments, the wide channel 30 may increase the stability with which the feature 22 may be secured to a base 20. Such stability may be helpful when a feature 22 comprises an indentation 24 or recess 24 positioned largely or entirely posterior to the corresponding teeth.

In selected embodiments, the width in the longitudinal direction 11a between opposing surfaces 32 of a channel 30 may be substantially constant across a feature 22 in the lateral direction 11b. That is, the width of the channel 30 may be substantially constant from one end of the channel 30 to the other. Alternatively, the width may vary. For example, in certain embodiments, a channel 30 may have the smallest width at the lateral 11b extremes thereof. The channel 30 may be the widest at a middle portion thereof.

In certain embodiments, curvature of the opposing surfaces 32 of a channel 30 may be complementary or track one another. For example, if a curved surface 32a corresponding to an anterior portion 34 of a feature 22 is primarily concave, then an opposing curved surface 32b corresponding to a posterior portion 36 of the feature 22 may be primarily convex. Alternatively, curvature of the opposing surfaces 32 of a channel 30 may be substantially opposite. For example, if a curved surface 32a corresponding to an anterior portion 34 of a feature 22 is primarily concave, then an opposing curved surface 32b corresponding to a posterior portion 36 of the feature 22 may also be primarily concave and extend away from the other surface 32a.

A channel 30 in accordance with the present invention may have any suitable floor 38 or ceiling 38 connecting the opposing curved surfaces 32 or sides. For example, a floor 38 or ceiling 38 may be substantially flat. Alternatively, a floor 38 or ceiling 38 may be curved (e.g., smoothly curving and transitioning from one curved surface 32a to the opposing curved surface 32b). In selected embodiments, a feature 22 corresponding to an indentation 24 or recess 24 may have a channel 30 with a floor 38 or ceiling 38 that is substantially flat, while a feature 22 corresponding to a protrusion 26 or mound 26 may have a channel 30 with a floor 38 or ceiling 38 that is smoothly curved as it transitions from one curved surface 32a to the opposing curved surface 32b.

The various edges and surfaces of a feature 22 may be radiused and smooth. Smooth, radiused edges and smooth surfaces may enhance the comfort experienced by a patient in wearing an appliance 10 in accordance with the present invention. For example, an upper lip of a patient may rest on an anterior portion 34 of a feature 22 of an upper portion 12 of an appliance 10. Accordingly, the anterior portion 34 may be radiused and smooth to avoid irritating or harming the tender tissues on the interior of the upper lip. Similarly, the tip of a tongue of a patient may rest on a posterior portion 36 of a feature 22 of an upper portion 12 of an appliance 10. Accordingly, the posterior portion 34 may be radiused and smooth to avoid irritating or harming the tongue of the patient.

Referring to FIGS. 12-19, a feature 22 providing or comprising a protrusion 26 or mound 26 may have any suitable configuration. In selected embodiments, such a feature 22 may include a first side having a convex surface 40 forming the protrusion 26 or mound 26. The feature 22 may also include a second side having an aperture 30 or channel 30 facilitating securement of the feature 22 to a base 20. In certain embodiments, such an aperture 30 or channel 30 may include one or more curved surfaces 32 that track or loosely follow a typically curve associated with an anterior area of a base 20.

Referring to FIGS. 20-25, in selected embodiments, as features 22 interact with one another, they may change a position of a lower jaw of a patient. For example, when lateral excursions (e.g., when a lower jaw moves side to side in the lateral direction 11b) take place, opposing features 22 may lessen the strain in the TMJ. That is, when directly contacting and opposing one another, the opposing features 22 may maintain a certain initial separation 42 between an upper and lower jaw. However, during a lateral excursion, a protrusion 26 may pass or move out of alignment with an opposing indentation 26. That is, a protrusion 26 may move along and "climb" the walls of an indentation 24. In a laterally misaligned position, a new, greater separation 44 between an upper and lower jaw may be applied or enforced. In certain embodiments or with certain patients, this greater separation 44 in a lateral excursion may lower the strain imposed on the TMJ.

Similarly, in certain embodiments during a longitudinal excursion (e.g., when a lower jaw moves in or out in the longitudinal direction 11a), a protrusion 26 may pass or move out of alignment with an opposing indentation 24. As with a lateral excursion, a longitudinal excursion may cause a protrusion 26 may move along and "climb" the walls of an indentation 24. Accordingly, in a longitudinally misaligned position, a new, greater separation 44 between an upper and lower jaw may also be applied or enforced.

Alternatively, one or both features 22 may be formed such that longitudinal excursions produce no significant change in the initial separation 42 between an upper and lower jaw. For example, an indentation 24 may form a channel extending longitudinally 11a through an corresponding feature 22. Thus, a lateral excursion may cause a protrusion 26 to contact and climb the sides of the channel to produce a greater spacing 44, while a longitudinal excursion may permit the protrusion 22 to simply slide along the channel without changing the initial spacing 42.

A protrusion 26 and indentation 24 in accordance with the present invention may have any suitable fit or relative size therebetween. For example, in selected embodiments, a protrusion 26 may be significantly thinner than an opposing indentation 24 in the longitudinal direction 11a, the lateral direction 11b, or both the longitudinal and lateral directions 11a, 11b. In such embodiments, a protrusion 26 may move within an opposing indentation 24 through a sizable range of motion in the longitudinal direction 11a, the lateral direction 11b, or both the longitudinal and lateral directions 11a, 11b, respectively.

Alternatively, a protrusion 26 may be closer to the size of an opposing indentation 24 in the longitudinal direction 11a, the lateral direction 11b, or both the longitudinal and lateral directions 11a, 11b. In such embodiments, a protrusion 26 may move within the indentation 24 through a smaller range of motion in the longitudinal direction 11a, the lateral direction 11b, or both the longitudinal and lateral directions 11a, 11b, respectively. In certain embodiments, a protrusion 26 may substantially match the size of an opposing indentation 24 in one or both of the longitudinal and lateral directions 11a, 11b. Thus, longitudinal and/or lateral excursions may only be permitted to the extent that the protrusion 26 exits the opposing indentation 24.

Accordingly, the relative sizing and shapes of a protrusion 26 and opposing indentation 24 may define to a certain degree the range of motion of a lower jaw with respect to an upper jaw. Additionally, in selected embodiments, the relative sizing and shapes of a protrusion 26 and opposing indentation 24 may define or generate a biasing force urging a lower jaw into a particular alignment (e.g., a neutral and/or centered alignment) with an upper jaw. For example, the sides of an indentation 24 may bias an opposing protrusion 26 toward a center of the indentation 24. That is, if a protrusion 22 is contacting the sides of an indentations 20 as shown in FIGS. 21, 22, 24, 25, forces of occlusion may result in a centering force 46 urging a lower jaw to return to a desired (e.g., a neutral and/or centered) alignment.

In selected embodiments, each feature 22 and the surfaces 28, 40 thereof may extend gradually and smoothly from the surrounding area of the respective portions 12, 16. Accordingly, in such embodiments, when in contact with one another, opposing features 22 may move smoothly over one another (e.g., in lateral excursions, longitudinal excursions, or both lateral and longitudinal excursions).

Indentations 24 and protrusions 26 in accordance with the present invention may have any suitable depth 48 and height 50, respectively. In selected embodiments, the depth 48 of a particular indentation 24 may be less than or substantially equal to the height 50 of a corresponding protrusion 26. In certain embodiments, the height 50 of a protrusion 26 may be in a range from about 1 mm to about 12 mm and preferably from about 3 mm to about 8 mm. In such embodiments, the depth 48 of an indentation 24 may also be in a range from about 1 mm to about 12 mm and preferably from about 3 mm to about 8 mm.

Similarly, indentations 24 and protrusions 26 in accordance with the present invention may have any suitable base widths 52, 54, respectively. In selected embodiments, the base width 52 of a particular indentation 24 in both the longitudinal and lateral directions 11a, 11b may be greater than or substantially equal to the base width 54 of a corresponding protrusion 26 in both the longitudinal and lateral directions 11a, 11b.

In certain embodiments, the base width 54 of a protrusion 26 in the lateral direction 11b may be in a range from about 2 mm to about 15 mm and preferably from about 5 mm to about 10 mm. In such embodiments, the base width 52 of an indentation 24 in the lateral direction 11b may be in a range from about 3 mm to about 30 mm and preferably from about 10 mm to about 20 mm.

In certain embodiments, the base width 54 of a protrusion 26 in the longitudinal direction 11a may be less than the base width 52 of an indentation 24 in the lateral direction 11b. For example, the base width 54 of a protrusion 26 in the longitudinal direction 11a may be in a range from about 2 mm to about 12 mm and preferably from about 5 mm to about 8 mm. In such embodiments, the base width 52 of an indentation 24 in the longitudinal direction may be in a range from about 3 mm to about 20 mm and preferably from about 8 mm to about 15 mm.

Referring to FIGS. 26-31, in certain alternative embodiments, an appliance 10 may include two opposing protrusions 26 or mounds 26, one on the anterior section of each portion 12, 16. When an appliance 10 is in place, opposing protrusions 26 on the anterior sections of the upper and lower portions 12, 16 may form an initial, primary, or exclusive point of contact between an upper jaw and a lower jaw. This may cause all forces of occlusion to be directed to the front of the mouth or to the front teeth and, therefore, prevent a patient from clenching or grinding teeth and provide to the patient the benefits associated therewith.

In selected embodiments, opposing protrusions 26 may change a position of a lower jaw. For example, when lateral excursions take place, opposing protrusions 26 may lessen the strain in the TMJ. That is, when directly contacting and opposing one another, two protrusions 26 may maintain a certain initial separation 56 between an upper and lower jaw. However, during a lateral excursion, one protrusion 26a may pass or move out of alignment with the other protrusion 26b. That is, one protrusion 26a may slide off of the other protrusion 26b. In an misaligned position, a new, lower separation 58 between an upper and lower jaw may be allowed or permitted. In certain embodiments or applications, or with certain patients, a lower separation 58 may lower the strain imposed on the TMJ in a lateral excursion.

In certain embodiments, during a longitudinal excursion, one protrusion 26a may pass or move out of alignment with the other protrusion 26b. In an misaligned position, a new, lower separation 58 between an upper and lower jaw may be allowed or permitted. Alternatively, one or both protrusions 26 may be formed such that longitudinal excursions produce no new or lower separation 58 between an upper and lower jaw.

In selected embodiments, each protrusion 26 may extend gradually and smoothly from the surrounding area of the respective portions 12, 16. Accordingly, in such embodiments, when in contact with one another, opposing protrusions 26 may move smoothly over one another (e.g., in lateral excursions, longitudinal excursions, or both lateral and longitudinal excursions).

Protrusions 26 in accordance with the present invention may have any suitable height 60. In selected embodiments, opposing protrusions 26a, 26b may have different heights 60a, 60b. Alternatively, the heights 60a, 60b of the opposing protrusions 26a, 26b may be equal. In certain embodiments, the height 60 of each protrusion 26 may be in a range from about 1 mm to about 6 mm and preferably from about 3 mm to about 6 mm. The width (e.g., base width) of each protrusion 26 may be in a range from about 5 mm to about 20 mm and preferably from about 10 mm to about 15 mm.

An appliance 10 with opposing protrusions 26 may be manufactured in any suitable manner. In selected embodiments, impressions of a patient's teeth may be taken, models of patient's teeth may be fabricated, and then polymeric material (e.g., acrylic sheets) may be applied to and/or formed around the modeled teeth to form appropriate bases 20. Protrusions 26 may then be positioned appropriately and bonded to the bases 20 on the anterior area thereof.

Bonding a protrusion 26 to a base 20 may be done by bonding on a feature 22 manufactured as separate, standardized piece. Alternatively, a feature 22 and corresponding protrusion 26 may be formed by hand from a polymeric material, epoxy, or the like that is molten, in a softened condition, uncured, or the like and urged against or otherwise bonded to a base 20.

In selected embodiments, a protrusion 26a corresponding to an upper portion 12 may be positioned differently than a protrusion 26b corresponding to a lower portion 16. This difference may ensure that the two protrusions 26a, 26b properly align when a lower jaw is in a desired position (e.g., a neutral position). For example, in certain embodiments, a protrusion 26a corresponding to an upper portion 12 may be positioned primarily behind the maxillary central incisors, while a protrusion 26b corresponding to a lower portion 16 may be positioned primarily over or just slightly behind the mandibular central incisors.

Referring to FIGS. 32-36, an appliance 10 in accordance with the present invention may be beneficially used by a patient suffering from bruxism, sleep apnea, or both bruxism and sleep apnea. For example, as noted above, an appliance 10 may include a first feature 22a comprising an indentation 24 or recess 24 and a second feature 22b comprising a protrusion 26 or mound 26. (Alternatively, a first feature 22a may comprise a protrusion 26 or mound 24 and a second feature 22b may comprise an indentation 24 or recess 24.) Interaction of such features 22a, 22b may be helpful in treating bruxism, sleep apnea, or both bruxism and sleep apnea.

For example, as noted above, such features 22a, 22b may be located on or secured to anterior areas of the respective first and second bases 20a, 20b. Moreover, the first and second features 22a, 22b may be shaped, sized, or position such that contact therebetween may be or comprise an initial, primary, or exclusive point of contact for forces of occlusion or the like passing from mandibular teeth to maxillary teeth of the corresponding patient. As a result, an appliance 10 may cause all forces of occlusion to be directed to the front of the mouth or to the front teeth. The brain of a patient may not allow the muscles of mastication to produce the same force of occlusion when pressure is only on the front teeth. Thus, an appliance may 10 may prevent a patient from clenching or grinding teeth and provide to the patient the benefits associated therewith.

Alternatively, or in addition thereto, such features 22a, 22b may urge a lower jaw to a position that reduces the incidence of sleep apnea. That is, interaction or nesting of the complementary concave and convex surfaces the features 22a, 22b and the centering forces 46 associated therewith may bias or guide a lower jaw of the corresponding patient to a desired position. As noted above, this desired position may be selected to open the airway of the patient, thereby decreasing snoring and reducing the incidence or symptoms of sleep apnea.

In certain embodiments, the ability of an appliance 10 in accordance to the present invention to treat sleep apnea may be enhanced through the addition of one or more biasing members 62. A biasing member 62 may apply a force to a lower jaw of a patient. The biasing member 62 may be oriented such that the force applied thereby may tend to maintain a protrusion 22b properly centered within an opposing indentation 22a. Thus, a biasing member 62 may assist opposing features 22a, 22b in maintaining the lower jaw of the patient in the desired position.

A biasing member 62 in accordance with the present invention may have any suitable shape and composition. In selected embodiments, a biasing member 62 may be formed of an elastomeric material. In such embodiments, when a biasing member 62 is stretched from its neutral position, a return or restorative force may be generated and used to maintain the lower jaw of the patient in the desired position.

In selected embodiments, a biasing member 62 may apply a force to a lower jaw of a patient by applying a force to a lower portion 16 worn by the patient. For example, a biasing member 62 may extend from an upper portion 12 worn by the patient to a lower portion 16 worn by the patient. In so doing, a biasing member 62 may connect to the upper and lower portions 12, 16 in any suitable manner. For example, in selected embodiments, the upper and lower portions 12, 16 may include engagement mechanisms 64 extending to engage one or more biasing members 62.

An engagement mechanism 64 may have any suitable configuration. In certain embodiments, the configuration of one or more engagement mechanisms 64 may be dictated by the configuration of one or more biasing members 62 corresponding thereof. For example, in selected embodiments, a biasing member 62 may include one or more (e.g., a series of) apertures 66. Accordingly, an engagement mechanism 64 may comprise an extension 68 (e.g., a post, hook, or the like) that may extend into an aperture 66, one end of an aperture 66, or the like to engage the corresponding biasing member 62. In certain embodiments, the edges of such an extension 68 may be chamfered, rounded, or the like to reduce or prevent any irritation or injury to the interior of the patient's mouth.

An engagement mechanism 64 may be connected to a corresponding upper or lower portion 12, 16 in any suitable manner. For example, in selected embodiments, an engagement mechanism 64 (e.g., an extension 68) may monolithically formed as part of a base 20, feature 22, or the like. Alternatively, an engagement mechanism 64 (e.g., extension 68) may be bonded onto a base 20, feature 22, or the like. Accordingly, in selected embodiments, an engagement mechanism 64 may include one or more features facilitating such bonding.

For example, in selected embodiments, an engagement mechanism 64 may comprise an extension 68 and a flange 70 connected to a base of the extension 68. The flange 70 may provide a larger surface area for bonding and increase the strength with which a corresponding engagement mechanism 64 may be bonded to an upper or lower portion 12, 16. In selected embodiments, one or more engagement mechanisms 64 may each comprise an extension 68 and corresponding flange 70 monolithically formed from a single piece of metal or metal alloy. An appliance 10 in accordance with the present invention may have any suitable number of engagement mechanisms 64 and corresponding biasing members 62. Moreover, the engagement mechanisms 64 and corresponding one or more biasing members 62 may be located, oriented, or the like to applied desired force or forces to the lower jaw of the patient.

For example, in selected embodiments, an appliance 10 may include four engagement mechanisms 64 and two biasing members 62. Two engagement mechanisms 64 and one biasing member 62 may be positioned on each side of the appliance 10. The two engagement mechanisms 64 (one on each of the upper and lower portions 12, 16) and the biasing member 62 extending therebetween may be located and oriented to urge a lower jaw forward and toward an upper jaw.

Figure 35:
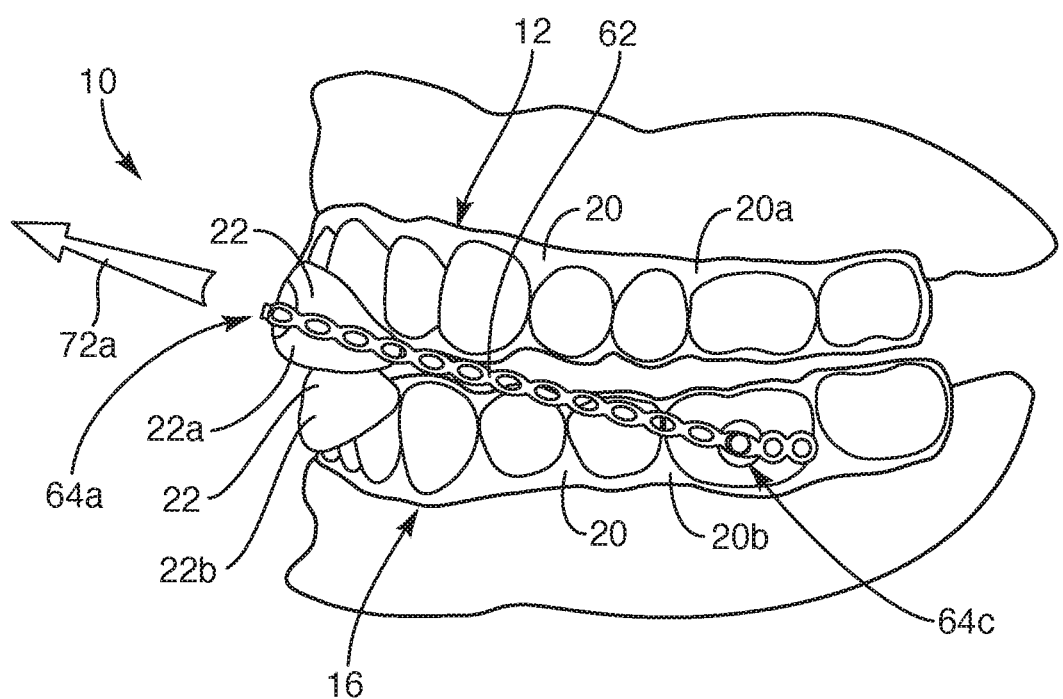
FIG. 35 is a side view of the dental appliance of FIG. 34 with the biasing member of FIG. 33 applied thereto in accordance with the present invention.
Figure 36:
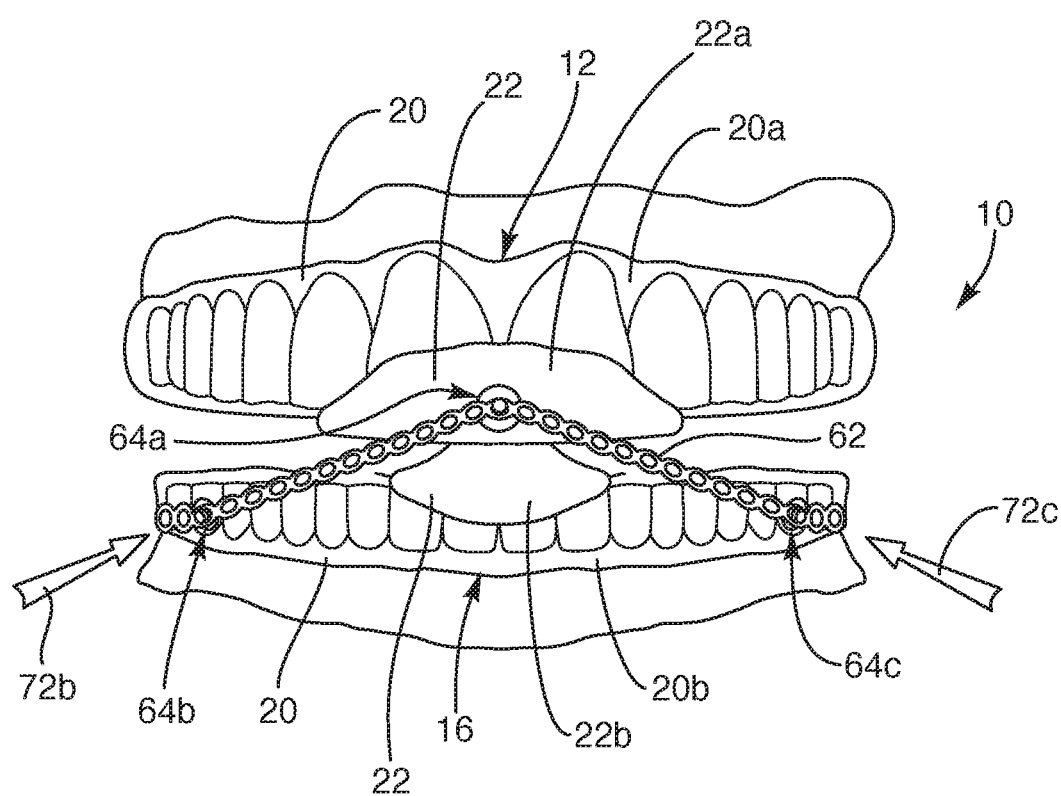
FIG. 36 is a front view of the dental appliance of FIG. 34 with the biasing member of FIG. 33 applied thereto in accordance with the present invention.

Alternatively, an appliance 10 may include three engagement mechanisms 64a, 64b, 64c. A first engagement mechanism 64a may be positioned on an anterior area (e.g., front and lateral center) of an upper portion 12. A second engagement mechanism 64b may be positioned on a right, posterior portion of a lower portion 16. A third engagement mechanism 64c may be positioned on a left, posterior portion of the lower portion 16. A first biasing member 62 may extend from the first engagement mechanism 64a to the second engagement mechanism 64b, while a second biasing member 62 may extend from the first engagement mechanism 64a to the third engagement mechanism 64c. Alternatively, the first and second biasing members 62 may comprise a single, monolithic, biasing member 62 extending from the second engagement mechanism 64b to the first engagement mechanism 64b to the third engagement mechanism 64c. For example, as shown in FIGS. 35 and 36, an extension 68 of a first engagement mechanism 64a may be inserted into an aperture 66 of a biasing member 62 (e.g., an aperture 66 proximate a midpoint of a biasing member 62) in order to create a mechanical interference therebetween that pins or anchors (e.g., laterally anchors or anchors with respect to side-to-side movement) that portion of the biasing member 62 to the first engagement mechanism 64a.

The force applied by such an arrangement of engagement mechanisms 64a, 64b, 64c, and biasing member 62 or biasing members 62 to a lower jaw may have various components 72. A first component 72a may tend to urge a lower jaw forward (in an anterior direction) and toward an upper jaw. Opposing second and third components 72b, 72c may tend to center a lower jaw with respect to an upper jaw.

The tension, pre-stretch, or the like in the one or more biasing mechanisms 62 may be selected to maintain a desired position, even when the patient relaxes his or her jaw muscles. Additionally, the biasing members 62 may not be so tight (or have such a high spring constant or short elongation limit) as to make the patient feel that his or her mouth is tied shut or overly restrained. A proper amount of force may make the patient feel as if his or her lower jaw is simply floating in place.

U.S. Pat. No. 6,666,212 issued Dec. 23, 2003 is hereby incorporated by reference.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for relieving symptoms related to sleep apnea, the method comprising:
    obtaining a dental appliance comprising
        an upper portion comprising a first base and a first feature, the first base shaped to engage upper teeth of a patient, the first feature securing to an anterior area of the first base and comprising one of a protrusion and a concave surface forming a concavity,
        a first engagement mechanism located at a front, lateral center of the upper portion,
        a lower portion comprising a second base and a second feature, the second base shaped to engage lower teeth of the patient, the second feature securing to an anterior area of the first base and comprising the other of the protrusion and the concave surface,
        a second engagement mechanism located at a first side of the lower portion,
        a third engagement mechanism located at a second, opposite side of the lower portion, and
        at least one biasing member formed of an elastomeric material;
    applying the appliance to the patient so that
        the upper portion moves with the upper teeth,
        the lower portion moves with the lower teeth,
        the at least one biasing member engages each of the first, second, and third engagement mechanisms and extends from the second engagement mechanism to the first engagement mechanism and from the first engagement mechanism to the third engagement mechanism, and
        a mechanical interference between the at least one biasing member and the first engagement mechanism laterally anchors a portion of the at least one biasing member to the first engagement mechanism;
    biting, by the patient, down on the appliance;
    entering, by the protrusion during the biting, the concavity and abutting the concave surface at a point of contact; and
    transferring a majority of a force associated with the biting through the point of contact.

2. The method of claim 1, wherein the first and second bases each comprise polymeric material that follows contours of at least selected teeth of the patient.

3. The method of claim 2, wherein:
    the polymeric material corresponding to the first base follows contours of substantially all of the upper teeth of the patient; and
    the polymeric material corresponding to the second base follows contours of substantially all of the lower teeth of the patient.

4. The method of claim 1, wherein:
    the portion of the at least one biasing member comprises an aperture;
    the first engagement mechanism comprises an extension; and
    the mechanical interference comprises the extension extending into the aperture.

5. The method of claim 2, wherein the first and second features each comprise polymeric material.

6. The method of claim 5, wherein the first and second features are bonded to the first and second bases, respectively.

7. The method of claim 6, wherein the first base is positioned between the upper teeth and the first feature.

8. The method of claim 7, wherein the second base is positioned between the lower teeth and the second feature.

9. The method of claim 8, wherein:
    the first feature comprises the concave surface forming the concavity; and
    the second feature comprises the protrusion.

10. The method of claim 9, wherein:
    a majority of the concave surface forming the concavity is positioned posterior to maxillary central incisors of the patient; and
    a majority of the protrusion is positioned superior to mandibular central incisors of the patient.

11. A method for relieving symptoms related to sleep apnea, the method comprising:
    obtaining a dental appliance comprising
        an upper portion comprising a first base shaped to engage upper teeth of a patient,
        a lower portion comprising a second base shaped to engage lower teeth of the patient, and
        at least one biasing member formed of an elastomeric material;
    applying the appliance to the patient such that
        the upper portion moves with the upper teeth,
        the lower portion moves with the lower teeth,
        the at least one biasing member engages each of a first side of the lower portion, a front, lateral center of the upper portion, and a second, opposite side of the lower portion,
        the at least one biasing member extends from the first side to the front, lateral center and from the front, lateral center to the second, opposite side, and
        a portion of the at least one biasing member is laterally anchored to the front, lateral center; and
    urging, by the at least one biasing member after the applying, the lower portion toward the upper portion and in an anterior direction.

12. The method of claim 11, wherein the first and second bases each comprise polymeric material that follows contours of at least selected teeth of the patient.

13. The method of claim 12, wherein:
    the polymeric material corresponding to the first base follows contours of substantially all of the upper teeth of the patient; and
    the polymeric material corresponding to the second base follows contours of substantially all of the lower teeth of the patient.

14. The method of claim 11, wherein:
    the portion of the at least one biasing member comprises an aperture;
    the front, lateral center comprises an extension; and
    the extension extends into the aperture to laterally anchor the portion of the at least one biasing member to the front, lateral center.

15. The method of claim 11, wherein the at least one biasing member is continuous from the first side to the second, opposite side.

16. The method of claim 11, wherein the at least one biasing member comprises:
    a first biasing member extending from the first side to the front, lateral center; and
    a second biasing member, separate from the first biasing member, extending from the front, lateral center to the second, opposite side.

17. A method for relieving symptoms related to sleep apnea, the method comprising:
  obtaining a dental appliance comprising
    an upper portion,
    a first engagement mechanism located at a front, lateral center of the upper portion,
    a lower portion,
    a second engagement mechanism located at a first side of the lower portion,
    a third engagement mechanism located at a second, opposite side of the lower portion, and
    at least one biasing member formed of an elastomeric material;
  applying the appliance to a patient such that
    the upper portion engages and moves with upper teeth of the patient,
    the lower portion engages and moves with lower teeth of the patient,
    the at least one biasing member engages each of the first, second, and third engagement mechanisms and extends from the second engagement mechanism directly to the first engagement mechanism and from the first engagement mechanism directly to the third engagement mechanism, and
    a portion of the at least one biasing member is laterally anchored to the first engagement mechanism; and
  urging, by the at least one biasing member after the applying, the lower portion toward the upper portion and in an anterior direction.

18. The method of claim 17, wherein the at least one biasing member is continuous from the second engagement mechanism to the third engagement mechanism.

19. The method of claim 17, wherein the at least one biasing member comprises:
  a first biasing member extending from the second engagement mechanism to the first engagement mechanism; and
  a second biasing member, separate from the first biasing member, extending from the first engagement mechanism to the third engagement mechanism.

20. The method of claim 18, wherein:
  the portion of the at least one biasing member comprises an aperture located proximate a midpoint of the at least one biasing member;
  the first engagement mechanism comprises an extension; and
  the extension extends into the aperture to laterally anchor the portion of the at least one biasing member to the first engagement mechanism.

\* \* \* \* \*